United States Patent
Jackson

(10) Patent No.: US 10,258,382 B2
(45) Date of Patent: Apr. 16, 2019

(54) ROD-CORD DYNAMIC CONNECTION ASSEMBLIES WITH SLIDABLE BONE ANCHOR ATTACHMENT MEMBERS ALONG THE CORD

(76) Inventor: Roger P. Jackson, Prairie Village, KS (US)

(*) Notice: Subject to any disclaimer, the term of this patent is extended or adjusted under 35 U.S.C. 154(b) by 1125 days.

(21) Appl. No.: 12/148,465

(22) Filed: Apr. 18, 2008

(65) Prior Publication Data
US 2008/0319482 A1 Dec. 25, 2008

Related U.S. Application Data

(63) Continuation-in-part of application No. 12/006,460, filed on Jan. 3, 2008, now Pat. No. 8,475,498.

(60) Provisional application No. 60/927,111, filed on May 1, 2007, provisional application No. 60/922,465, filed on Apr. 9, 2007, provisional application No. 60/898,870, filed on Feb. 1, 2007, provisional application No. 60/880,969, filed on Jan. 18, 2007.

(51) Int. Cl.
*A61B 17/70* (2006.01)

(52) U.S. Cl.
CPC ........ *A61B 17/702* (2013.01); *A61B 17/7026* (2013.01); *A61B 17/7004* (2013.01)

(58) Field of Classification Search
CPC ..................................... A61B 17/70–17/7046
USPC .......................................... 606/246, 254–279
See application file for complete search history.

(56) References Cited

U.S. PATENT DOCUMENTS

| 854,956 A | 5/1907 | Martin |
| 2,243,717 A | 5/1941 | Moreira |
| 2,346,346 A | 4/1944 | Anderson |
| 2,362,999 A | 11/1944 | Elmer |
| 2,531,892 A | 11/1950 | Reese |
| 2,813,450 A | 11/1957 | Dzus |
| 3,013,244 A | 12/1961 | Rudy |
| 3,236,275 A | 2/1966 | Smith |
| 3,604,487 A | 9/1971 | Gilbert |
| 3,640,416 A | 2/1972 | Temple |
| 4,033,139 A | 7/1977 | Frederick |
| 4,041,939 A | 8/1977 | Hall |
| 4,190,091 A | 2/1980 | Colognori |
| 4,373,754 A | 2/1983 | Bollfrass et al. |

(Continued)

FOREIGN PATENT DOCUMENTS

| CA | 2577436 | 6/2006 |
| DE | 4239716 | 8/1994 |

(Continued)

OTHER PUBLICATIONS

Wang et al. "Viscoelastic characteristics of Shape memory polymers" Jun. 3, 2010, Journal of Applied polymer Science, vol. 118, issue 3, pp. 1406-1413.*

(Continued)

*Primary Examiner* — Nicholas J Plionis
*Assistant Examiner* — Steven J Cotroneo
(74) *Attorney, Agent, or Firm* — Polsinelli PC

(57) ABSTRACT

A dynamic fixation medical implant having at least two bone anchors includes a longitudinal connecting member assembly having a core portion made from at least one pre-tensioned flexible member and a cooperating pre-compressed surrounding outer sleeve. The sleeve surrounds the core and is disposed between cooperating rigid end members that are attached to the bone anchors.

52 Claims, 7 Drawing Sheets

(56) References Cited

U.S. PATENT DOCUMENTS

| | | |
|---|---|---|
| 4,448,191 A | 5/1984 | Rodnyansky et al. |
| 4,484,570 A | 11/1984 | Sutter et al. |
| 4,600,224 A | 7/1986 | Blose |
| 4,653,486 A | 3/1987 | Coker |
| 4,703,954 A | 11/1987 | Ortloff et al. |
| 4,707,001 A | 11/1987 | Johnson |
| 4,743,260 A | 5/1988 | Burton |
| 4,748,260 A | 5/1988 | Marlett |
| 4,759,672 A | 7/1988 | Nilsen et al. |
| 4,790,297 A | 12/1988 | Luque |
| 4,836,196 A | 6/1989 | Park et al. |
| 4,877,020 A | 10/1989 | Vich |
| 4,887,596 A | 12/1989 | Sherman |
| 4,946,458 A | 8/1990 | Harms et al. |
| 4,950,269 A | 8/1990 | Gaines, Jr. |
| 5,005,562 A | 4/1991 | Cotrel |
| 5,019,080 A | 5/1991 | Hemer |
| 5,020,519 A | 6/1991 | Hayes et al. |
| 5,022,791 A | 6/1991 | Isler |
| 5,034,011 A | 7/1991 | Howland |
| 5,042,982 A | 8/1991 | Harms et al. |
| 5,067,955 A | 11/1991 | Cotrel |
| 5,084,048 A | 1/1992 | Jacob et al. |
| 5,092,635 A | 3/1992 | DeLange et al. |
| 5,092,866 A | 3/1992 | Breard et al. |
| 5,102,412 A | 4/1992 | Rogozinski |
| 5,129,388 A | 7/1992 | Vignaud et al. |
| 5,147,363 A | 9/1992 | Harle |
| 5,154,719 A | 10/1992 | Cotrel |
| 5,176,483 A | 1/1993 | Baumann et al. |
| 5,176,678 A | 1/1993 | Tsou |
| 5,176,679 A | 1/1993 | Lin |
| 5,176,680 A | 1/1993 | Vignaud et al. |
| 5,180,393 A | 1/1993 | Commarmond |
| 5,207,678 A | 5/1993 | Harms et al. |
| 5,217,497 A | 6/1993 | Mehdian |
| 5,257,993 A | 11/1993 | Asher et al. |
| 5,261,907 A | 11/1993 | Vignaud et al. |
| 5,261,912 A | 11/1993 | Frigg |
| 5,275,601 A | 1/1994 | Gogolewski et al. |
| 5,282,863 A | 2/1994 | Burton |
| D346,217 S | 4/1994 | Sparker et al. |
| 5,306,275 A | 4/1994 | Bryan |
| 5,312,404 A | 5/1994 | Asher et al. |
| 5,321,901 A | 6/1994 | Kelly |
| 5,346,493 A | 9/1994 | Stahurski et al. |
| 5,358,289 A | 10/1994 | Banker et al. |
| 5,360,431 A | 11/1994 | Puno et al. |
| 5,375,823 A | 12/1994 | Navas |
| 5,385,583 A | 1/1995 | Cotrel |
| 5,395,371 A | 3/1995 | Miller et al. |
| 5,409,488 A | 4/1995 | Ulrich |
| 5,409,489 A | 4/1995 | Sioufi |
| 5,414,661 A | 5/1995 | Holmes |
| 5,415,661 A | 5/1995 | Holmes |
| 5,423,816 A | 6/1995 | Lin |
| 5,427,418 A | 6/1995 | Watts |
| 5,429,639 A | 7/1995 | Judet |
| 5,443,467 A | 8/1995 | Biedermann et al. |
| 5,466,237 A | 11/1995 | Byrd, III et al. |
| 5,466,238 A | 11/1995 | Lin |
| 5,468,241 A | 11/1995 | Metz-Stavenhagen et al. |
| 5,474,555 A | 12/1995 | Puno et al. |
| 5,476,462 A | 12/1995 | Allard et al. |
| 5,476,464 A | 12/1995 | Metz-Stavenhagen et al. |
| 5,480,401 A | 1/1996 | Navas |
| 5,484,437 A | 1/1996 | Michelson |
| 5,484,440 A | 1/1996 | Allard |
| 5,487,742 A | 1/1996 | Cotrel |
| 5,489,307 A | 2/1996 | Kuslich et al. |
| 5,490,750 A | 2/1996 | Gundy |
| 5,499,892 A | 3/1996 | Reed |
| 5,505,731 A | 4/1996 | Tornier |
| 5,507,745 A | 4/1996 | Logroscino et al. |
| 5,496,321 A | 5/1996 | Puno |
| 5,540,688 A | 7/1996 | Navas |
| 5,545,165 A | 8/1996 | Biedermann et al. |
| 5,549,607 A | 8/1996 | Olson et al. |
| 5,554,157 A | 9/1996 | Errico et al. |
| 5,562,660 A | 10/1996 | Grob |
| 5,562,663 A | 10/1996 | Wisnewski et al. |
| 5,569,247 A | 10/1996 | Morrison |
| 5,569,251 A | 10/1996 | Baker et al. |
| 5,584,834 A | 12/1996 | Errico et al. |
| 5,586,984 A | 12/1996 | Errico et al. |
| 5,591,166 A | 1/1997 | Bernhardt et al. |
| 5,601,553 A | 2/1997 | Trebing et al. |
| 5,607,304 A | 3/1997 | Bailey et al. |
| 5,607,425 A | 3/1997 | Rogozinski |
| 5,607,426 A | 3/1997 | Ralph et al. |
| 5,607,428 A | 3/1997 | Lin |
| 5,611,800 A | 3/1997 | Davis et al. |
| 5,628,740 A | 5/1997 | Mullane |
| 5,630,817 A | 5/1997 | Rokegem |
| 5,641,256 A | 6/1997 | Gundy |
| 5,643,260 A | 7/1997 | Doherty |
| 5,643,261 A | 7/1997 | Schafer et al. |
| 5,647,873 A | 7/1997 | Errico et al. |
| 5,662,652 A | 9/1997 | Schafer et al. |
| 5,662,653 A | 9/1997 | Songer et al. |
| 5,669,909 A | 9/1997 | Zdeblick et al. |
| 5,669,911 A | 9/1997 | Errico et al. |
| 5,672,175 A | 9/1997 | Martin |
| 5,672,176 A | 9/1997 | Biedermann et al. |
| 5,676,703 A | 10/1997 | Gelbard |
| 5,681,319 A | 10/1997 | Biedermann et al. |
| 5,683,390 A | 11/1997 | Metz-Stavenhagen et al. |
| 5,690,630 A | 11/1997 | Errico et al. |
| 5,697,929 A | 12/1997 | Mellinger |
| 5,711,709 A | 1/1998 | McCoy |
| 5,713,898 A | 2/1998 | Stucker et al. |
| 5,716,356 A | 2/1998 | Biedermann et al. |
| 5,720,751 A | 2/1998 | Jackson |
| 5,723,013 A | 3/1998 | Jeanson et al. |
| 5,725,527 A | 3/1998 | Biedermann et al. |
| 5,725,528 A | 3/1998 | Biedermann et al. |
| 5,728,098 A | 3/1998 | Sherman et al. |
| 5,733,286 A | 3/1998 | Errico et al. |
| 5,738,685 A | 4/1998 | Halm et al. |
| 5,741,254 A | 4/1998 | Henry et al. |
| 5,752,957 A | 5/1998 | Ralph et al. |
| 5,782,830 A | 7/1998 | Farris |
| 5,782,833 A | 7/1998 | Haider |
| 5,792,044 A | 8/1998 | Foley et al. |
| 5,797,911 A | 8/1998 | Sherman et al. |
| 5,800,435 A | 9/1998 | Errico et al. |
| 5,800,547 A | 9/1998 | Schafer et al. |
| 5,810,816 A | 9/1998 | Roussouly et al. |
| 5,817,094 A | 10/1998 | Errico et al. |
| 5,863,293 A | 1/1999 | Richelsoph |
| 5,873,878 A | 2/1999 | Harms et al. |
| 5,876,402 A | 3/1999 | Errico et al. |
| 5,879,350 A | 3/1999 | Sherman et al. |
| 5,879,351 A | 3/1999 | Viart |
| 5,882,350 A | 3/1999 | Ralph et al. |
| 5,885,286 A | 3/1999 | Sherman et al. |
| 5,891,145 A | 4/1999 | Morrison et al. |
| 5,902,231 A | 5/1999 | Foley et al. |
| RE36,221 E | 6/1999 | Breard et al. |
| 5,910,141 A | 6/1999 | Morrison et al. |
| 5,938,663 A | 8/1999 | Petreto |
| 5,944,465 A | 8/1999 | Janitzki |
| 5,951,553 A | 9/1999 | Betz |
| 5,954,725 A | 9/1999 | Sherman et al. |
| 5,961,517 A | 10/1999 | Biedermann et al. |
| 5,964,760 A | 10/1999 | Richetsoph |
| 6,001,098 A | 12/1999 | Metz-Stavenhagen et al. |
| 6,004,349 A | 12/1999 | Jackson |
| 6,010,503 A | 1/2000 | Richetsoph et al. |
| 6,019,759 A | 2/2000 | Rogozinski |
| 6,022,350 A | 2/2000 | Ganem |
| 6,053,917 A | 4/2000 | Sherman et al. |
| 6,059,786 A | 5/2000 | Jackson |
| 6,063,090 A | 5/2000 | Schlapfer |

(56) References Cited

U.S. PATENT DOCUMENTS

| | | | |
|---|---|---|---|
| 6,074,391 A | 6/2000 | Metz-Stavenhagen et al. | |
| 6,077,262 A | 6/2000 | Schlapfer et al. | |
| 6,086,588 A | 7/2000 | Ameil et al. | |
| 6,090,110 A | 7/2000 | Metz-Stavenhagen | |
| 6,090,111 A | 7/2000 | Nichols | |
| 6,099,528 A | 8/2000 | Seurat | |
| 6,102,912 A | 8/2000 | Cazin et al. | |
| 6,102,913 A | 8/2000 | Jackson | |
| 6,110,172 A | 8/2000 | Jackson | |
| 6,113,601 A | 9/2000 | Tatar | |
| 6,117,137 A | 9/2000 | Halm et al. | |
| 6,132,431 A * | 10/2000 | Nilsson et al. | 606/261 |
| 6,132,432 A | 10/2000 | Richelsoph | |
| 6,132,434 A | 10/2000 | Sherman et al. | |
| 6,136,002 A | 10/2000 | Shih et al. | |
| 6,139,549 A | 10/2000 | Keller | |
| 6,143,032 A | 11/2000 | Schafer et al. | |
| 6,146,383 A | 11/2000 | Studer et al. | |
| 6,183,472 B1 | 2/2001 | Lutz | |
| 6,186,718 B1 | 2/2001 | Fogard | |
| 6,187,005 B1 | 2/2001 | Brace et al. | |
| 6,193,720 B1 | 2/2001 | Yuan et al. | |
| 6,214,012 B1 | 4/2001 | Karpman et al. | |
| RE37,161 E | 5/2001 | Michelson et al. | |
| 6,224,596 B1 | 5/2001 | Brace et al. | |
| 6,224,598 B1 | 5/2001 | Jackson | |
| 6,235,028 B1 | 5/2001 | Brumfield et al. | |
| 6,235,034 B1 | 5/2001 | Bray | |
| 6,241,730 B1 | 6/2001 | Alby | |
| 6,248,105 B1 | 6/2001 | Schlapfer et al. | |
| 6,248,107 B1 | 6/2001 | Foley et al. | |
| 6,251,112 B1 | 6/2001 | Jackson | |
| 6,254,146 B1 | 7/2001 | Church | |
| 6,254,602 B1 | 7/2001 | Justis | |
| 6,267,764 B1 | 7/2001 | Elberg | |
| 6,267,765 B1 | 7/2001 | Taylor et al. | |
| 6,273,888 B1 | 8/2001 | Justis | |
| 6,277,122 B1 | 8/2001 | McGahan et al. | |
| 6,280,442 B1 | 8/2001 | Barker et al. | |
| 6,280,445 B1 | 8/2001 | Morrison et al. | |
| 6,287,308 B1 | 9/2001 | Betz et al. | |
| 6,287,311 B1 | 9/2001 | Sherman et al. | |
| 6,290,700 B1 | 9/2001 | Schmotzer | |
| 6,296,642 B1 | 10/2001 | Morrison et al. | |
| 6,296,643 B1 | 10/2001 | Hopf et al. | |
| 6,299,613 B1 | 10/2001 | Ogilvie et al. | |
| 6,302,888 B1 | 10/2001 | Mellinger et al. | |
| 6,309,391 B1 | 10/2001 | Crandall et al. | |
| 6,315,564 B1 | 11/2001 | Levisman | |
| 6,315,779 B1 | 11/2001 | Morrison et al. | |
| 6,331,179 B1 | 12/2001 | Freid et al. | |
| 6,355,040 B1 | 3/2002 | Richelsoph et al. | |
| RE37,665 E | 4/2002 | Ralph et al. | |
| 6,368,321 B1 | 4/2002 | Jackson | |
| 6,371,957 B1 | 4/2002 | Amrein et al. | |
| 6,402,752 B2 | 6/2002 | Schaffler-Wachter et al. | |
| 6,402,757 B1 | 6/2002 | Moore et al. | |
| 6,440,133 B1 | 8/2002 | Beale et al. | |
| 6,440,137 B1 | 8/2002 | Horvath et al. | |
| 6,443,956 B1 | 9/2002 | Ray | |
| 6,451,021 B1 | 9/2002 | Ralph et al. | |
| 6,471,703 B1 | 10/2002 | Ashman | |
| 6,471,705 B1 | 10/2002 | Biedermann et al. | |
| 6,478,801 B1 | 11/2002 | Ralph et al. | |
| 6,485,491 B1 | 11/2002 | Farris et al. | |
| 6,485,492 B1 | 11/2002 | Halm et al. | |
| 6,485,494 B1 | 11/2002 | Haider | |
| 6,488,681 B2 | 12/2002 | Martin et al. | |
| 6,508,818 B2 | 1/2003 | Steiner et al. | |
| 6,511,484 B2 | 1/2003 | Torode et al. | |
| 6,520,962 B1 | 2/2003 | Taylor et al. | |
| 6,527,804 B1 | 3/2003 | Gauchet et al. | |
| 6,530,929 B1 | 3/2003 | Justis et al. | |
| 6,533,786 B1 | 3/2003 | Needham et al. | |
| 6,539,826 B2 | 4/2003 | Oesterle et al. | |
| 6,540,749 B2 | 4/2003 | Schafer et al. | |
| 6,547,790 B2 | 4/2003 | Harkey, III et al. | |
| 6,551,320 B2 | 4/2003 | Lieberman | |
| 6,551,323 B2 | 4/2003 | Doubler et al. | |
| 6,554,831 B1 | 4/2003 | Rivard et al. | |
| 6,554,832 B2 | 4/2003 | Shtuzas | |
| 6,554,834 B2 | 4/2003 | Crozet et al. | |
| 6,558,387 B2 | 5/2003 | Errico et al. | |
| 6,562,038 B1 | 5/2003 | Morrison | |
| 6,562,040 B1 | 5/2003 | Wagner | |
| 6,565,565 B1 | 5/2003 | Yuan et al. | |
| 6,565,567 B1 | 5/2003 | Haider | |
| 6,572,618 B1 | 6/2003 | Morrison | |
| 6,582,436 B2 | 6/2003 | Schlapfer et al. | |
| 6,582,466 B1 | 6/2003 | Gaucher | |
| 6,585,740 B2 | 7/2003 | Schlapfer et al. | |
| 6,595,992 B1 | 7/2003 | Wagner et al. | |
| 6,595,993 B2 | 7/2003 | Doono et al. | |
| 6,599,294 B2 | 7/2003 | Fuss et al. | |
| 6,610,063 B2 | 8/2003 | Kumar et al. | |
| 6,613,050 B1 | 9/2003 | Wagner et al. | |
| 6,616,667 B1 | 9/2003 | Steiger et al. | |
| 6,616,669 B2 | 9/2003 | Ogilvie | |
| 6,623,485 B2 | 9/2003 | Doubler et al. | |
| 6,626,347 B2 | 9/2003 | Ng | |
| 6,626,907 B2 | 9/2003 | Campbell et al. | |
| 6,626,908 B2 | 9/2003 | Cooper et al. | |
| 6,635,059 B2 | 10/2003 | Randall et al. | |
| 6,635,060 B2 | 10/2003 | Hanson et al. | |
| 6,648,885 B1 | 11/2003 | Friesem | |
| 6,648,887 B2 | 11/2003 | Ashman | |
| 6,648,888 B1 | 11/2003 | Shluzas | |
| 6,652,526 B1 | 11/2003 | Arafiles | |
| 6,652,765 B1 | 11/2003 | Beaty | |
| 6,656,179 B1 | 12/2003 | Schaefer et al. | |
| 6,656,181 B2 | 12/2003 | Dixon et al. | |
| 6,660,004 B2 | 12/2003 | Barker et al. | |
| 6,660,006 B2 | 12/2003 | Markworth et al. | |
| 6,663,632 B1 | 12/2003 | Frigg | |
| 6,663,635 B2 | 12/2003 | Frigg et al. | |
| 6,673,073 B1 | 1/2004 | Schafer | |
| 6,676,661 B1 | 1/2004 | Martin Benlloch et al. | |
| 6,679,833 B2 | 1/2004 | Smith et al. | |
| 6,682,529 B2 | 1/2004 | Stahurski | |
| 6,682,530 B2 | 1/2004 | Dixon et al. | |
| 6,689,133 B2 | 2/2004 | Morrison et al. | |
| 6,689,134 B2 | 2/2004 | Ralph et al. | |
| 6,695,843 B2 | 2/2004 | Biedermann et al. | |
| 6,695,851 B2 | 2/2004 | Zdeblick et al. | |
| 6,699,249 B2 | 3/2004 | Schlapfer et al. | |
| 6,706,045 B2 | 3/2004 | Lin et al. | |
| 6,712,818 B1 | 3/2004 | Michelson | |
| 6,716,213 B2 | 4/2004 | Shitoto | |
| 6,716,214 B1 | 4/2004 | Jackson | |
| 6,716,247 B2 | 4/2004 | Michelson | |
| 6,723,100 B2 | 4/2004 | Biedermann et al. | |
| 6,730,093 B2 | 5/2004 | Saint Martin | |
| 6,730,127 B2 | 5/2004 | Michelson | |
| 6,733,502 B2 | 5/2004 | Altarac et al. | |
| 6,736,816 B2 | 5/2004 | Ritland | |
| 6,736,820 B2 | 5/2004 | Biedermann et al. | |
| 6,740,086 B2 | 5/2004 | Richelsoph | |
| 6,743,231 B1 | 6/2004 | Gray et al. | |
| 6,746,449 B2 | 6/2004 | Jones et al. | |
| 6,746,454 B2 | 6/2004 | Winterbottom et al. | |
| 6,755,829 B1 | 6/2004 | Bono et al. | |
| 6,755,835 B2 | 6/2004 | Schultheiss et al. | |
| 6,755,836 B1 | 6/2004 | Lewis | |
| 6,761,723 B2 | 7/2004 | Buttermann et al. | |
| 6,767,351 B2 | 7/2004 | Orbay et al. | |
| 6,770,075 B2 | 8/2004 | Howland | |
| 6,780,186 B2 | 8/2004 | Errico et al. | |
| 6,783,527 B2 | 8/2004 | Drewry et al. | |
| 6,790,208 B2 | 9/2004 | Oribe et al. | |
| 6,790,209 B2 | 9/2004 | Beale et al. | |
| 6,802,844 B2 | 10/2004 | Ferree | |
| 6,827,719 B2 | 12/2004 | Ralph et al. | |
| 6,830,571 B2 | 12/2004 | Lenke et al. | |
| 6,835,196 B2 | 12/2004 | Biedermann et al. | |

(56) References Cited

U.S. PATENT DOCUMENTS

| | | |
|---|---|---|
| 6,837,889 B2 | 1/2005 | Shluzas |
| 6,840,940 B2 | 1/2005 | Ralph et al. |
| 6,843,791 B2 | 1/2005 | Serhan |
| 6,857,343 B1 | 2/2005 | Easterbrooks et al. |
| 6,858,031 B2 | 2/2005 | Morrison et al. |
| 6,869,432 B2 | 3/2005 | Schlapfer et al. |
| 6,869,433 B2 | 3/2005 | Glascott |
| 6,872,208 B1 | 3/2005 | McBride et al. |
| 6,896,676 B2 | 5/2005 | Zubok et al. |
| 6,932,817 B2 | 8/2005 | Baynham et al. |
| 6,932,820 B2 | 8/2005 | Osman |
| 6,945,972 B2 | 9/2005 | Frigg et al. |
| 6,953,462 B2 | 10/2005 | Lieberman |
| 6,955,677 B2 | 10/2005 | Dahners |
| 6,958,065 B2 | 10/2005 | Ueyarra et al. |
| 6,964,664 B2 | 11/2005 | Freid et al. |
| 6,964,665 B2 | 11/2005 | Thomas et al. |
| 6,964,667 B2 | 11/2005 | Shaolian et al. |
| 6,966,910 B2 | 11/2005 | Ritland |
| 6,974,460 B2 | 12/2005 | Carbone et al. |
| 6,979,334 B2 | 12/2005 | Dalton |
| 6,981,973 B2 | 1/2006 | McKinley |
| 6,986,771 B2 | 1/2006 | Paul et al. |
| 6,989,011 B2 | 1/2006 | Paul et al. |
| 6,991,632 B2 | 1/2006 | Ritland |
| 7,044,947 B2 | 2/2006 | Shluzus et al. |
| RE39,035 E | 3/2006 | Finn et al. |
| 7,008,422 B2 | 3/2006 | Foley et al. |
| 7,008,424 B2 | 3/2006 | Teitelbaum |
| 7,011,660 B2 | 3/2006 | Sherman et al. |
| 7,018,378 B2 | 3/2006 | Biedermann et al. |
| 7,018,379 B2 | 3/2006 | Drewry et al. |
| 7,022,122 B2 | 4/2006 | Amrein et al. |
| 7,029,475 B2 | 4/2006 | Panjabi |
| RE39,089 E | 5/2006 | Ralph et al. |
| 7,052,497 B2 | 5/2006 | Sherman et al. |
| 7,056,321 B2 | 6/2006 | Pagliuca et al. |
| 7,066,062 B2 | 6/2006 | Flesher |
| 7,066,937 B2 | 6/2006 | Shluzas |
| 7,081,116 B1 | 7/2006 | Carly |
| 7,083,621 B2 | 8/2006 | Shaolian et al. |
| 7,087,057 B2 | 8/2006 | Konieczynski et al. |
| 7,090,674 B2 | 8/2006 | Doubler et al. |
| 7,090,679 B2 | 8/2006 | Saint-Martin et al. |
| 7,090,680 B2 | 8/2006 | Bonati et al. |
| 7,094,242 B2 | 8/2006 | Ralph et al. |
| 7,118,576 B2 | 10/2006 | Gitis et al. |
| 7,121,755 B2 | 10/2006 | Schlapfer et al. |
| 7,125,410 B2 | 10/2006 | Freudiger |
| 7,125,426 B2 | 10/2006 | Moumene et al. |
| 7,128,743 B2 | 10/2006 | Metz-Stavenhagen |
| 7,137,985 B2 | 11/2006 | Jahng |
| 7,141,051 B2 | 11/2006 | Janowski et al. |
| 7,144,396 B2 | 12/2006 | Shluzas |
| 7,163,538 B2 | 1/2007 | Altarac et al. |
| 7,163,539 B2 | 1/2007 | Abdelgany et al. |
| 7,166,108 B2 | 1/2007 | Mazda et al. |
| 7,179,261 B2 | 2/2007 | Sicvol et al. |
| 7,186,255 B2 | 3/2007 | Baynham et al. |
| 7,188,626 B2 | 3/2007 | Foley et al. |
| 7,207,991 B2 | 4/2007 | Michelson |
| 7,207,992 B2 | 4/2007 | Ritland |
| 7,211,085 B2 | 5/2007 | Michelson |
| 7,211,086 B2 | 5/2007 | Biedermann et al. |
| 7,211,087 B2 | 5/2007 | Young |
| 7,214,227 B2 | 5/2007 | Colleran et al. |
| 7,223,268 B2 | 5/2007 | Biedermann |
| 7,229,441 B2 | 6/2007 | Trieu et al. |
| 7,264,621 B2 | 9/2007 | Coates et al. |
| 7,270,665 B2 | 9/2007 | Morrison et al. |
| 7,282,064 B2 | 10/2007 | Chin |
| 7,291,151 B2 | 11/2007 | Alvarez |
| 7,291,153 B2 | 11/2007 | Glascott |
| 7,294,127 B2 | 11/2007 | Hawkins et al. |
| 7,294,128 B2 | 11/2007 | Alleyne et al. |
| 7,294,129 B2 | 11/2007 | Hawkins et al. |
| 7,306,603 B2 | 12/2007 | Boehm, Jr. et al. |
| 7,306,604 B2 | 12/2007 | Carli |
| 7,306,606 B2 | 12/2007 | Sasing |
| 7,314,467 B2 | 1/2008 | Howland |
| 7,316,684 B1 | 1/2008 | Baccelli et al. |
| 7,322,979 B2 | 1/2008 | Crandall et al. |
| 7,329,258 B2 | 2/2008 | Studer |
| 7,335,201 B2 | 2/2008 | Doubler et al. |
| 7,335,202 B2 | 2/2008 | Matthis et al. |
| 7,338,490 B2 | 3/2008 | Ogilvie et al. |
| 7,338,491 B2 | 3/2008 | Baker et al. |
| 7,361,196 B2 | 4/2008 | Fallin et al. |
| 7,377,921 B2 | 5/2008 | Studer et al. |
| 7,476,238 B2 | 1/2009 | Panjabi |
| 7,491,208 B2 | 2/2009 | Pond, Jr. et al. |
| 7,556,639 B2 | 7/2009 | Rothman et al. |
| 7,559,942 B2 | 7/2009 | Paul et al. |
| 7,563,274 B2 | 7/2009 | Justis et al. |
| 7,563,283 B2 | 7/2009 | Kwak |
| 7,588,589 B2 | 9/2009 | Falahee |
| 7,601,166 B2 | 10/2009 | Biedermann et al. |
| 7,604,653 B2 | 10/2009 | Kitchen |
| 7,604,654 B2 | 10/2009 | Fallin et al. |
| 7,611,518 B2 | 11/2009 | Walder et al. |
| 7,615,068 B2 | 11/2009 | Timm et al. |
| 7,621,912 B2 | 11/2009 | Harms et al. |
| 7,621,940 B2 | 11/2009 | Harms et al. |
| 7,625,393 B2 | 12/2009 | Fallin et al. |
| 7,632,292 B2 | 12/2009 | Sengupta et al. |
| 7,641,673 B2 | 1/2010 | LeCouedic et al. |
| 7,651,515 B2 | 1/2010 | Mack et al. |
| 7,655,026 B2 | 2/2010 | Justis et al. |
| 7,658,739 B2 | 2/2010 | Shluzas |
| 7,658,752 B2 | 2/2010 | Labrom et al. |
| 7,682,375 B2 | 3/2010 | Ritland |
| 7,695,496 B2 | 4/2010 | Labrom et al. |
| 7,695,498 B2 | 4/2010 | Ritland |
| 7,695,514 B2 | 4/2010 | Kwak |
| 7,713,288 B2 * | 5/2010 | Timm et al. .................. 606/257 |
| 7,763,048 B2 | 7/2010 | Fortin et al. |
| 7,763,052 B2 | 7/2010 | Jahng |
| 7,766,941 B2 | 8/2010 | Paul |
| 7,766,942 B2 | 8/2010 | Patterson et al. |
| 7,766,943 B1 | 8/2010 | Fallin et al. |
| 7,776,071 B2 | 8/2010 | Fortin et al. |
| 7,776,075 B2 | 8/2010 | Bruneau et al. |
| 7,785,349 B2 | 8/2010 | Walder et al. |
| 7,785,351 B2 | 8/2010 | Gordon et al. |
| 7,794,480 B2 | 9/2010 | Gordon et al. |
| 7,806,913 B2 | 10/2010 | Fanger et al. |
| 7,811,309 B2 | 10/2010 | Timm et al. |
| 7,815,663 B2 | 10/2010 | Trieu |
| 7,815,664 B2 | 10/2010 | Sherman et al. |
| 7,815,665 B2 * | 10/2010 | Jahng et al. .................. 606/263 |
| 7,828,825 B2 | 11/2010 | Bruneau et al. |
| 7,842,072 B2 | 11/2010 | Dawson |
| 7,901,437 B2 | 3/2011 | Jackson |
| 7,988,710 B2 | 8/2011 | Jahng et al. |
| 8,128,667 B2 | 3/2012 | Jackson |
| 8,157,843 B2 | 4/2012 | Biederman et al. |
| 8,292,926 B2 | 10/2012 | Jackson |
| 8,366,745 B2 | 2/2013 | Jackson |
| 9,101,404 B2 | 8/2015 | Jackson |
| 9,439,683 B2 | 9/2016 | Jackson |
| 9,451,989 B2 | 9/2016 | Jackson |
| 9,861,394 B2 | 1/2018 | Jackson |
| 2001/0001119 A1 | 5/2001 | Lombardo |
| 2001/0010000 A1 | 7/2001 | Gertzbein |
| 2001/0023350 A1 | 9/2001 | Choi |
| 2001/0029375 A1 | 10/2001 | Betz |
| 2001/0037111 A1 | 11/2001 | Dixon et al. |
| 2002/0007184 A1 | 1/2002 | Ogilvie et al. |
| 2002/0013586 A1 | 1/2002 | Justis et al. |
| 2002/0035360 A1 | 3/2002 | Connors et al. |
| 2002/0035366 A1 | 3/2002 | Walder et al. |
| 2002/0045898 A1 | 4/2002 | Freid et al. |
| 2002/0055740 A1 * | 5/2002 | Lieberman .................. 606/61 |
| 2002/0058942 A1 | 5/2002 | Biedermann et al. |

(56) References Cited

U.S. PATENT DOCUMENTS

| | | |
|---|---|---|
| 2002/0068975 A1 | 6/2002 | Teitelbaum et al. |
| 2002/0072751 A1 | 6/2002 | Jackson |
| 2002/0077701 A1 | 6/2002 | Kuslich |
| 2002/0082602 A1 | 6/2002 | Biedermann et al. |
| 2002/0095153 A1 | 7/2002 | Jones et al. |
| 2002/0107570 A1* | 8/2002 | Sybert et al. ............... 623/13.17 |
| 2002/0111626 A1 | 8/2002 | Ralph et al. |
| 2002/0116001 A1 | 8/2002 | Schafer |
| 2002/0116065 A1 | 8/2002 | Jackson |
| 2002/0133159 A1 | 9/2002 | Jackson |
| 2002/0143341 A1 | 10/2002 | Biedermann et al. |
| 2002/0173789 A1 | 11/2002 | Howland |
| 2002/0193795 A1 | 12/2002 | Gertzbein et al. |
| 2002/0198526 A1 | 12/2002 | Shaolian et al. |
| 2003/0023240 A1 | 1/2003 | Amrein et al. |
| 2003/0023243 A1 | 1/2003 | Biedermann et al. |
| 2003/0073996 A1 | 4/2003 | Doubler et al. |
| 2003/0083657 A1 | 5/2003 | Drewry et al. |
| 2003/0093078 A1 | 5/2003 | Ritland |
| 2003/0100896 A1 | 5/2003 | Biedermann et al. |
| 2003/0105460 A1 | 6/2003 | Crandall et al. |
| 2003/0109880 A1 | 6/2003 | Shirado et al. |
| 2003/0114852 A1 | 6/2003 | Biedermann et al. |
| 2003/0125741 A1 | 7/2003 | Biedermann et al. |
| 2003/0149432 A1 | 8/2003 | Frigg et al. |
| 2003/0153911 A1 | 8/2003 | Shluzas |
| 2003/0163133 A1 | 8/2003 | Altarac et al. |
| 2003/0171749 A1 | 9/2003 | Le Douedic et al. |
| 2003/0176862 A1 | 9/2003 | Taylor et al. |
| 2003/0191470 A1 | 10/2003 | Ritland |
| 2003/0199873 A1 | 10/2003 | Richelsoph |
| 2003/0208203 A1 | 11/2003 | Lim et al. |
| 2003/0208204 A1 | 11/2003 | Bailey et al. |
| 2003/0212398 A1 | 11/2003 | Jackson |
| 2003/0216735 A1 | 11/2003 | Altarac et al. |
| 2003/0220642 A1 | 11/2003 | Freudiger |
| 2003/0220643 A1 | 11/2003 | Ferree |
| 2003/0225408 A1 | 12/2003 | Nichols et al. |
| 2004/0002708 A1 | 1/2004 | Ritland |
| 2004/0006342 A1 | 1/2004 | Altarac et al. |
| 2004/0049189 A1 | 3/2004 | Le Couedic et al. |
| 2004/0049190 A1 | 3/2004 | Biedermann et al. |
| 2004/0073215 A1 | 4/2004 | Carli |
| 2004/0078082 A1 | 4/2004 | Lange |
| 2004/0220671 A1 | 4/2004 | Ralph et al. |
| 2004/0087949 A1 | 5/2004 | Bono et al. |
| 2004/0087952 A1 | 5/2004 | Borgstrom et al. |
| 2004/0092934 A1 | 5/2004 | Howland |
| 2004/0097933 A1 | 5/2004 | Lourdel et al. |
| 2004/0116929 A1 | 6/2004 | Barker et al. |
| 2004/0133207 A1 | 7/2004 | Abdou |
| 2004/0138662 A1 | 7/2004 | Landry et al. |
| 2004/0143265 A1 | 7/2004 | Landry et al. |
| 2004/0147928 A1 | 7/2004 | Landry et al. |
| 2004/0147929 A1 | 7/2004 | Biedermann et al. |
| 2004/0158247 A1 | 8/2004 | Sitiso et al. |
| 2004/0162560 A1 | 8/2004 | Raynor et al. |
| 2004/0167523 A1 | 8/2004 | Jackson |
| 2004/0172022 A1 | 9/2004 | Landry et al. |
| 2004/0172032 A1 | 9/2004 | Jackson |
| 2004/0176766 A1 | 9/2004 | Shluzas |
| 2004/0186473 A1 | 9/2004 | Cournoyer et al. |
| 2004/0210216 A1 | 10/2004 | Farris et al. |
| 2004/0215191 A1 | 10/2004 | Kitchen |
| 2004/0220567 A1 | 11/2004 | Eisermann et al. |
| 2004/0225289 A1 | 11/2004 | Biedermann et al. |
| 2004/0236327 A1 | 11/2004 | Paul et al. |
| 2004/0236328 A1 | 11/2004 | Paul et al. |
| 2004/0236329 A1 | 11/2004 | Panjabi |
| 2004/0236330 A1 | 11/2004 | Purcell et al. |
| 2004/0249380 A1 | 12/2004 | Glascott |
| 2004/0260283 A1 | 12/2004 | Wu et al. |
| 2004/0267264 A1 | 12/2004 | Konieczynski et al. |
| 2005/0010220 A1 | 1/2005 | Casutt et al. |
| 2005/0027296 A1 | 2/2005 | Thramann et al. |
| 2005/0033298 A1 | 2/2005 | Hawkes et al. |
| 2005/0038432 A1 | 2/2005 | Shaolian et al. |
| 2005/0049708 A1 | 3/2005 | Atkinson et al. |
| 2005/0055026 A1 | 3/2005 | Biedermann et al. |
| 2005/0065514 A1 | 3/2005 | Studer |
| 2005/0065515 A1 | 3/2005 | Jahng |
| 2005/0065516 A1 | 3/2005 | Jahng |
| 2005/0065517 A1 | 3/2005 | Chin |
| 2005/0070899 A1 | 3/2005 | Doubler et al. |
| 2005/0080415 A1 | 4/2005 | Keyer et al. |
| 2005/0085812 A1 | 4/2005 | Sherman |
| 2005/0085813 A1 | 4/2005 | Spitler et al. |
| 2005/0085815 A1 | 4/2005 | Harms et al. |
| 2005/0085816 A1 | 4/2005 | Michelson |
| 2005/0096652 A1 | 5/2005 | Burton |
| 2005/0096654 A1 | 5/2005 | Lin |
| 2005/0107788 A1 | 5/2005 | Beaurain et al. |
| 2005/0113927 A1 | 5/2005 | Malek |
| 2005/0124991 A1 | 6/2005 | Jahng |
| 2005/0131404 A1 | 6/2005 | Mazda et al. |
| 2005/0131407 A1 | 6/2005 | Sicvol et al. |
| 2005/0131413 A1 | 6/2005 | O'Driscoll et al. |
| 2005/0137597 A1 | 6/2005 | Butler et al. |
| 2005/0143737 A1 | 6/2005 | Pafford et al. |
| 2005/0143823 A1 | 6/2005 | Boyd et al. |
| 2005/0149020 A1 | 7/2005 | Jahng |
| 2005/0149023 A1 | 7/2005 | Ritland |
| 2005/0154389 A1 | 7/2005 | Selover et al. |
| 2005/0154390 A1 | 7/2005 | Biedermann et al. |
| 2005/0154391 A1 | 7/2005 | Doherty et al. |
| 2005/0159750 A1 | 7/2005 | Doherty |
| 2005/0165396 A1 | 7/2005 | Fortin et al. |
| 2005/0165400 A1 | 7/2005 | Fernandez |
| 2005/0171540 A1 | 8/2005 | Lim et al. |
| 2005/0171543 A1 | 8/2005 | Timm et al. |
| 2005/0177157 A1 | 8/2005 | Jahng |
| 2005/0182401 A1 | 8/2005 | Timm et al. |
| 2005/0187548 A1 | 8/2005 | Butler et al. |
| 2005/0187555 A1 | 8/2005 | Biedermann et al. |
| 2005/0192571 A1 | 9/2005 | Abdelgany |
| 2005/0192580 A1 | 9/2005 | Dalton |
| 2005/0203511 A1 | 9/2005 | Wilson-MacDonald et al. |
| 2005/0203513 A1 | 9/2005 | Jahng et al. |
| 2005/0203514 A1* | 9/2005 | Jahng ............... A61B 17/1757 606/263 |
| 2005/0203516 A1 | 9/2005 | Biedermann et al. |
| 2005/0203517 A1 | 9/2005 | Jahng et al. |
| 2005/0203518 A1 | 9/2005 | Biedermann et al. |
| 2005/0203519 A1 | 9/2005 | Harms et al. |
| 2005/0216001 A1 | 9/2005 | David |
| 2005/0216003 A1 | 9/2005 | Biedermann et al. |
| 2005/0228501 A1 | 10/2005 | Miller et al. |
| 2005/0234450 A1 | 10/2005 | Barker |
| 2005/0234451 A1 | 10/2005 | Markworth |
| 2005/0234452 A1 | 10/2005 | Malandain |
| 2005/0234453 A1 | 10/2005 | Shaolian et al. |
| 2005/0234454 A1 | 10/2005 | Chin |
| 2005/0234456 A1 | 10/2005 | Malandain |
| 2005/0240181 A1 | 10/2005 | Boomer et al. |
| 2005/0240183 A1 | 10/2005 | Vaughan |
| 2005/0245930 A1 | 11/2005 | Timm et al. |
| 2005/0251137 A1 | 11/2005 | Ball |
| 2005/0251139 A1 | 11/2005 | Roh |
| 2005/0251140 A1 | 11/2005 | Shaolian et al. |
| 2005/0251141 A1 | 11/2005 | Frigg et al. |
| 2005/0260058 A1 | 11/2005 | Casagne, III |
| 2005/0261685 A1 | 11/2005 | Fortin et al. |
| 2005/0261687 A1 | 11/2005 | Garamszegi et al. |
| 2005/0267470 A1 | 12/2005 | McBride |
| 2005/0267471 A1 | 12/2005 | Biedermann et al. |
| 2005/0267474 A1 | 12/2005 | Dalton |
| 2005/0267477 A1 | 12/2005 | Jackson |
| 2005/0273099 A1 | 12/2005 | Baccelli et al. |
| 2005/0273101 A1 | 12/2005 | Schumacher |
| 2005/0277919 A1 | 12/2005 | Slivka et al. |
| 2005/0277920 A1 | 12/2005 | Slivka et al. |
| 2005/0277922 A1 | 12/2005 | Trieu et al. |
| 2005/0277923 A1 | 12/2005 | Sweeney |
| 2005/0277925 A1 | 12/2005 | Mujwid |

(56) References Cited

U.S. PATENT DOCUMENTS

| | | |
|---|---|---|
| 2005/0277927 A1 | 12/2005 | Guenther et al. |
| 2005/0277928 A1 | 12/2005 | Boschert |
| 2005/0277931 A1 | 12/2005 | Sweeney et al. |
| 2005/0277932 A1 | 12/2005 | Farris |
| 2005/0277934 A1 | 12/2005 | Vardiman |
| 2005/0283152 A1 | 12/2005 | Lindemann et al. |
| 2005/0283157 A1 | 12/2005 | Coates et al. |
| 2005/0283238 A1 | 12/2005 | Reiley |
| 2005/0283244 A1 | 12/2005 | Gordon et al. |
| 2005/0288669 A1 | 12/2005 | Abdou |
| 2005/0288670 A1 | 12/2005 | Panjabi et al. |
| 2005/0288671 A1 | 12/2005 | Yuan et al. |
| 2005/0288672 A1 | 12/2005 | Ferree |
| 2005/0288673 A1 | 12/2005 | Catbagan et al. |
| 2006/0004357 A1 | 1/2006 | Lee et al. |
| 2006/0004359 A1 | 1/2006 | Kramer et al. |
| 2006/0004360 A1 | 1/2006 | Kramer et al. |
| 2006/0004363 A1 | 1/2006 | Brockmeyer et al. |
| 2006/0009767 A1 | 1/2006 | Kiester |
| 2006/0009768 A1 | 1/2006 | Ritland |
| 2006/0009769 A1 | 1/2006 | Lieberman |
| 2006/0009770 A1 | 1/2006 | Speirs et al. |
| 2006/0009775 A1 | 1/2006 | Dec et al. |
| 2006/0009780 A1 | 1/2006 | Foley et al. |
| 2006/0009846 A1 | 1/2006 | Trieu et al. |
| 2006/0015099 A1 | 1/2006 | Cannon et al. |
| 2006/0015104 A1 | 1/2006 | Dalton |
| 2006/0025767 A1 | 2/2006 | Khalili |
| 2006/0025768 A1 | 2/2006 | Iott et al. |
| 2006/0025770 A1 | 2/2006 | Schlapfer et al. |
| 2006/0030850 A1 | 2/2006 | Keegan et al. |
| 2006/0036240 A1 | 2/2006 | Colleran et al. |
| 2006/0036242 A1 | 2/2006 | Nilsson et al. |
| 2006/0036244 A1 | 2/2006 | Spitler et al. |
| 2006/0036246 A1 | 2/2006 | Carl et al. |
| 2006/0036252 A1 | 2/2006 | Baynham et al. |
| 2006/0036254 A1 | 2/2006 | Lim |
| 2006/0036256 A1 | 2/2006 | Carl et al. |
| 2006/0036259 A1 | 2/2006 | Carl et al. |
| 2006/0036260 A1 | 2/2006 | Runco et al. |
| 2006/0036323 A1 | 2/2006 | Carl et al. |
| 2006/0036324 A1 | 2/2006 | Sachs et al. |
| 2006/0041259 A1 | 2/2006 | Paul et al. |
| 2006/0052780 A1 | 3/2006 | Errico et al. |
| 2006/0052783 A1 | 3/2006 | Dant et al. |
| 2006/0052784 A1 | 3/2006 | Dant et al. |
| 2006/0052786 A1 | 3/2006 | Dant et al. |
| 2006/0058788 A1 | 3/2006 | Hammer et al. |
| 2006/0058790 A1 | 3/2006 | Carl et al. |
| 2006/0064090 A1* | 3/2006 | Park .................. 606/61 |
| 2006/0064091 A1 | 3/2006 | Ludwig et al. |
| 2006/0064092 A1 | 3/2006 | Howland |
| 2006/0069390 A1 | 3/2006 | Frigg |
| 2006/0074419 A1 | 4/2006 | Taylor et al. |
| 2006/0079894 A1 | 4/2006 | Colleran et al. |
| 2006/0079895 A1 | 4/2006 | McLeer |
| 2006/0079896 A1 | 4/2006 | Kwak |
| 2006/0079898 A1 | 4/2006 | Ainsworth |
| 2006/0079899 A1 | 4/2006 | Ritland |
| 2006/0084977 A1 | 4/2006 | Lieberman |
| 2006/0084981 A1 | 4/2006 | Shluzas |
| 2006/0084982 A1 | 4/2006 | Kim |
| 2006/0084983 A1 | 4/2006 | Kim |
| 2006/0084984 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0084989 A1 | 4/2006 | Dickinson et al. |
| 2006/0084991 A1 | 4/2006 | Borgslrom |
| 2006/0084993 A1 | 4/2006 | Landry et al. |
| 2006/0084995 A1 | 4/2006 | Biedermann et al. |
| 2006/0085069 A1 | 4/2006 | Kim |
| 2006/0089643 A1 | 4/2006 | Mujwid |
| 2006/0089644 A1 | 4/2006 | Felix |
| 2006/0095037 A1 | 5/2006 | Jones et al. |
| 2006/0106380 A1 | 5/2006 | Colleran et al. |
| 2006/0106381 A1 | 5/2006 | Ferree |
| 2006/0106383 A1 | 5/2006 | Biedermann et al. |
| 2006/0111714 A1 | 5/2006 | Foley |
| 2006/0111715 A1 | 5/2006 | Jackson |
| 2006/0116677 A1 | 6/2006 | Burd et al. |
| 2006/0122597 A1 | 6/2006 | Jojnes et al. |
| 2006/0122599 A1 | 6/2006 | Drewry |
| 2006/0129147 A1 | 6/2006 | Biedermann et al. |
| 2006/0129149 A1 | 6/2006 | Iott et al. |
| 2006/0129239 A1 | 6/2006 | Kwak |
| 2006/0142758 A1 | 6/2006 | Petit |
| 2006/0142760 A1* | 6/2006 | McDonnell .................. 606/61 |
| 2006/0142761 A1 | 6/2006 | Landry et al. |
| 2006/0149228 A1 | 7/2006 | Schlapter |
| 2006/0149229 A1 | 7/2006 | Kwak |
| 2006/0149232 A1 | 7/2006 | Sasing |
| 2006/0149238 A1 | 7/2006 | Sherman et al. |
| 2006/0149241 A1 | 7/2006 | Richelsoph et al. |
| 2006/0149244 A1 | 7/2006 | Amrein et al. |
| 2006/0155277 A1 | 7/2006 | Metz-Stavenhagen |
| 2006/0155278 A1 | 7/2006 | Warnick |
| 2006/0161152 A1 | 7/2006 | Ensign et al. |
| 2006/0167454 A1 | 7/2006 | Ludwig et al. |
| 2006/0167455 A1 | 7/2006 | Clement et al. |
| 2006/0173454 A1 | 8/2006 | Spitler et al. |
| 2006/0173456 A1 | 8/2006 | Hawkes et al. |
| 2006/0184171 A1 | 8/2006 | Biedermann |
| 2006/0184180 A1 | 8/2006 | Augostino |
| 2006/0189983 A1 | 8/2006 | Faliln |
| 2006/0189984 A1 | 8/2006 | Fallin |
| 2006/0189985 A1 | 8/2006 | Lewis |
| 2006/0195090 A1 | 8/2006 | Suddaby |
| 2006/0195093 A1 | 8/2006 | Jahng |
| 2006/0195198 A1 | 8/2006 | Schumacher |
| 2006/0200123 A1 | 9/2006 | Mueller |
| 2006/0200130 A1 | 9/2006 | Hawkins |
| 2006/0200131 A1 | 9/2006 | Chao et al. |
| 2006/0200132 A1 | 9/2006 | Chao et al. |
| 2006/0200135 A1 | 9/2006 | Sherman et al. |
| 2006/0200138 A1 | 9/2006 | Michelson |
| 2006/0200139 A1 | 9/2006 | Michelson |
| 2006/0200149 A1 | 9/2006 | Hoy et al. |
| 2006/0210494 A1 | 9/2006 | Rabiei et al. |
| 2006/0212033 A1 | 9/2006 | Rothman |
| 2006/0212034 A1 | 9/2006 | Triplett et al. |
| 2006/0217713 A1 | 9/2006 | Serhan et al. |
| 2006/0217714 A1 | 9/2006 | Serhan et al. |
| 2006/0217715 A1 | 9/2006 | Albert et al. |
| 2006/0217716 A1 | 9/2006 | Baker et al. |
| 2006/0229608 A1 | 10/2006 | Foster |
| 2006/0229609 A1 | 10/2006 | Wang |
| 2006/0229612 A1 | 10/2006 | Rothman |
| 2006/0229613 A1 | 10/2006 | Timm |
| 2006/0229614 A1 | 10/2006 | Foley et al. |
| 2006/0229615 A1 | 10/2006 | Abdou |
| 2006/0235389 A1 | 10/2006 | Albert et al. |
| 2006/0235392 A1 | 10/2006 | Hammer et al. |
| 2006/0235393 A1 | 10/2006 | Bono et al. |
| 2006/0241593 A1 | 10/2006 | Sherman et al. |
| 2006/0241595 A1 | 10/2006 | Molz, IV et al. |
| 2006/0241599 A1 | 10/2006 | Konieczynski et al. |
| 2006/0241600 A1 | 10/2006 | Ensign et al. |
| 2006/0241602 A1 | 10/2006 | Jackson |
| 2006/0241603 A1 | 10/2006 | Jackson |
| 2006/0241769 A1 | 10/2006 | Gordon |
| 2006/0241771 A1 | 10/2006 | Gordon |
| 2006/0247624 A1 | 11/2006 | Banouskou et al. |
| 2006/0247630 A1 | 11/2006 | Iott et al. |
| 2006/0247631 A1 | 11/2006 | Ahn et al. |
| 2006/0247633 A1 | 11/2006 | Winslow |
| 2006/0247635 A1 | 11/2006 | Gordon |
| 2006/0247636 A1 | 11/2006 | Yuan et al. |
| 2006/0247637 A1 | 11/2006 | Colleran |
| 2006/0247779 A1 | 11/2006 | Gordon |
| 2006/0264933 A1 | 11/2006 | Baker et al. |
| 2006/0264934 A1 | 11/2006 | Fallin |
| 2006/0264935 A1 | 11/2006 | White |
| 2006/0264936 A1 | 11/2006 | Partin et al. |

(56) References Cited

U.S. PATENT DOCUMENTS

| | | | |
|---|---|---|---|
| 2006/0264937 A1* | 11/2006 | White | A61B 17/702 606/257 |
| 2006/0264940 A1 | 11/2006 | Hartmann | |
| 2006/0264942 A1 | 11/2006 | Lim et al. | |
| 2006/0264962 A1 | 11/2006 | Chin et al. | |
| 2006/0269940 A1 | 11/2006 | Harman | |
| 2006/0276787 A1 | 12/2006 | Zubok et al. | |
| 2006/0276789 A1 | 12/2006 | Jackson | |
| 2006/0276791 A1 | 12/2006 | Shluzas | |
| 2006/0276792 A1 | 12/2006 | Ensign et al. | |
| 2006/0282074 A1 | 12/2006 | Renaud et al. | |
| 2006/0282075 A1 | 12/2006 | Labrom | |
| 2006/0282076 A1 | 12/2006 | Labrom | |
| 2006/0282077 A1 | 12/2006 | Labrom | |
| 2006/0282078 A1 | 12/2006 | Labrom | |
| 2006/0282079 A1 | 12/2006 | Labrom | |
| 2006/0282080 A1 | 12/2006 | Albert | |
| 2006/0293657 A1 | 12/2006 | Hartmann | |
| 2006/0293659 A1 | 12/2006 | Alvarez | |
| 2006/0293663 A1 | 12/2006 | Walkenhorst | |
| 2006/0293665 A1 | 12/2006 | Shluzas | |
| 2006/0293666 A1 | 12/2006 | Matthis et al. | |
| 2007/0005062 A1 | 1/2007 | Lange | |
| 2007/0005063 A1 | 1/2007 | Bruneau et al. | |
| 2007/0005137 A1 | 1/2007 | Kwak | |
| 2007/0016188 A1 | 1/2007 | Boehm, Jr. et al. | |
| 2007/0016190 A1 | 1/2007 | Martinez | |
| 2007/0016193 A1 | 1/2007 | Ritland | |
| 2007/0016194 A1 | 1/2007 | Shaolian et al. | |
| 2007/0016198 A1 | 1/2007 | Boehm, Jr. et al. | |
| 2007/0016199 A1 | 1/2007 | Boehm, Jr. et al. | |
| 2007/0021750 A1 | 1/2007 | Shluzas et al. | |
| 2007/0032123 A1* | 2/2007 | Timm et al. | 439/395 |
| 2007/0043355 A1 | 2/2007 | Bette et al. | |
| 2007/0043356 A1 | 2/2007 | Timm | |
| 2007/0043357 A1 | 2/2007 | Kirschman | |
| 2007/0043358 A1 | 2/2007 | Molz, IV et al. | |
| 2007/0043359 A1 | 2/2007 | Altarac et al. | |
| 2007/0043364 A1 | 2/2007 | Cawley et al. | |
| 2007/0049931 A1 | 3/2007 | Justis et al. | |
| 2007/0049933 A1 | 3/2007 | Ahn et al. | |
| 2007/0049936 A1 | 3/2007 | Colleran | |
| 2007/0055235 A1 | 3/2007 | Janowski et al. | |
| 2007/0055236 A1 | 3/2007 | Hudgins | |
| 2007/0055238 A1 | 3/2007 | Biedermann et al. | |
| 2007/0055239 A1 | 3/2007 | Sweeney et al. | |
| 2007/0055240 A1 | 3/2007 | Matthis et al. | |
| 2007/0055241 A1 | 3/2007 | Matthis et al. | |
| 2007/0055242 A1 | 3/2007 | Bailly | |
| 2007/0055244 A1 | 3/2007 | Jackson | |
| 2007/0055247 A1 | 3/2007 | Jahng | |
| 2007/0073289 A1 | 3/2007 | Kwak | |
| 2007/0073290 A1 | 3/2007 | Boehm, Jr. | |
| 2007/0073291 A1 | 3/2007 | Cordaro et al. | |
| 2007/0073293 A1 | 3/2007 | Martz | |
| 2007/0073405 A1 | 3/2007 | Chin et al. | |
| 2007/0078460 A1 | 4/2007 | Frigg et al. | |
| 2007/0078461 A1 | 4/2007 | Shluzas | |
| 2007/0083199 A1 | 4/2007 | Baccelli | |
| 2007/0088357 A1 | 4/2007 | Johnson et al. | |
| 2007/0088359 A1 | 4/2007 | Woods et al. | |
| 2007/0093813 A1 | 4/2007 | Callahan, II et al. | |
| 2007/0093814 A1 | 4/2007 | Callahan, II et al. | |
| 2007/0093815 A1 | 4/2007 | Callahan, II et al. | |
| 2007/0093817 A1 | 4/2007 | Barrus et al. | |
| 2007/0093818 A1 | 4/2007 | Biedermann et al. | |
| 2007/0093819 A1 | 4/2007 | Albert | |
| 2007/0093824 A1 | 4/2007 | Hestad et al. | |
| 2007/0093826 A1 | 4/2007 | Hawkes et al. | |
| 2007/0093827 A1 | 4/2007 | Warnick | |
| 2007/0093828 A1 | 4/2007 | Abdou | |
| 2007/0093831 A1 | 4/2007 | Abdelgany et al. | |
| 2007/0093833 A1 | 4/2007 | Kuiper et al. | |
| 2007/0100341 A1* | 5/2007 | Reglos et al. | 606/61 |
| 2007/0118117 A1 | 5/2007 | Altarac et al. | |
| 2007/0118118 A1 | 5/2007 | Kwak et al. | |
| 2007/0118119 A1 | 5/2007 | Hestad | |
| 2007/0118122 A1 | 5/2007 | Butler et al. | |
| 2007/0118123 A1 | 5/2007 | Strausbaugh et al. | |
| 2007/0118124 A1 | 5/2007 | Biedermann et al. | |
| 2007/0123862 A1 | 5/2007 | Warnick | |
| 2007/0123864 A1* | 5/2007 | Walder et al. | 606/61 |
| 2007/0123865 A1 | 5/2007 | Schlapfer et al. | |
| 2007/0123866 A1 | 5/2007 | Gerbec et al. | |
| 2007/0123867 A1 | 5/2007 | Kirschman | |
| 2007/0123870 A1 | 5/2007 | Jeon et al. | |
| 2007/0123871 A1 | 5/2007 | Jahng | |
| 2007/0129729 A1* | 6/2007 | Petit et al. | 606/61 |
| 2007/0135815 A1 | 6/2007 | Gerbec et al. | |
| 2007/0161986 A1 | 7/2007 | Levy | |
| 2007/0161991 A1 | 7/2007 | Attarac et al. | |
| 2007/0161994 A1 | 7/2007 | Lowery et al. | |
| 2007/0161995 A1 | 7/2007 | Trautwein et al. | |
| 2007/0161996 A1 | 7/2007 | Biedermann et al. | |
| 2007/0161997 A1 | 7/2007 | Thramann et al. | |
| 2007/0161999 A1 | 7/2007 | Biedermann et al. | |
| 2007/0167948 A1 | 7/2007 | Abdou | |
| 2007/0167949 A1 | 7/2007 | Altarac et al. | |
| 2007/0173818 A1 | 7/2007 | Hestad et al. | |
| 2007/0173819 A1 | 7/2007 | Sandlin | |
| 2007/0173820 A1 | 7/2007 | Trieu | |
| 2007/0173822 A1 | 7/2007 | Bruneau et al. | |
| 2007/0173828 A1 | 7/2007 | Firkins et al. | |
| 2007/0173832 A1 | 7/2007 | Tebbe et al. | |
| 2007/0191839 A1 | 8/2007 | Justis et al. | |
| 2007/0191841 A1 | 8/2007 | Justis et al. | |
| 2007/0191846 A1 | 8/2007 | Bruneau et al. | |
| 2007/0198014 A1 | 8/2007 | Graf et al. | |
| 2007/0123720 A1 | 9/2007 | Gordon et al. | |
| 2007/0208344 A1 | 9/2007 | Young | |
| 2007/0213720 A1 | 9/2007 | Gordon et al. | |
| 2007/0225707 A1 | 9/2007 | Wisnewski et al. | |
| 2007/0225708 A1 | 9/2007 | Biedermann et al. | |
| 2007/0225710 A1 | 9/2007 | Jahng et al. | |
| 2007/0225711 A1 | 9/2007 | Ensign | |
| 2007/0233064 A1 | 10/2007 | Holt | |
| 2007/0233073 A1 | 10/2007 | Wisnewski et al. | |
| 2007/0233075 A1 | 10/2007 | Dawson | |
| 2007/0233078 A1 | 10/2007 | Justis et al. | |
| 2007/0233080 A1 | 10/2007 | Na et al. | |
| 2007/0233085 A1 | 10/2007 | Biedermann et al. | |
| 2007/0233086 A1 | 10/2007 | Harms et al. | |
| 2007/0233087 A1 | 10/2007 | Schlapfer | |
| 2007/0233092 A1 | 10/2007 | Falahee | |
| 2007/0233094 A1 | 10/2007 | Colleran et al. | |
| 2007/0233095 A1 | 10/2007 | Schlaepfer | |
| 2007/0250061 A1 | 10/2007 | Chin et al. | |
| 2007/0124249 A1 | 11/2007 | Lim et al. | |
| 2007/0260243 A1 | 11/2007 | Biedemann | |
| 2007/0270806 A1 | 11/2007 | Foley et al. | |
| 2007/0270807 A1 | 11/2007 | Armstrong et al. | |
| 2007/0270810 A1 | 11/2007 | Sanders | |
| 2007/0270813 A1 | 11/2007 | Garamszegi | |
| 2007/0270814 A1 | 11/2007 | Lim et al. | |
| 2007/0270815 A1 | 11/2007 | Johnson et al. | |
| 2007/0270821 A1 | 11/2007 | Trieu et al. | |
| 2007/0270830 A1 | 11/2007 | Morrison | |
| 2007/0270831 A1 | 11/2007 | Dewey et al. | |
| 2007/0270832 A1 | 11/2007 | Moore | |
| 2007/0270835 A1 | 11/2007 | Wisnewski | |
| 2007/0270837 A1 | 11/2007 | Eckhardt et al. | |
| 2007/0270838 A1 | 11/2007 | Bruneau et al. | |
| 2007/0270839 A1 | 11/2007 | Jeon et al. | |
| 2007/0270840 A1 | 11/2007 | Chin et al. | |
| 2007/0270843 A1 | 11/2007 | Matthis et al. | |
| 2007/0276380 A1* | 11/2007 | Jahng et al. | 606/61 |
| 2007/0288004 A1 | 12/2007 | Alvarez | |
| 2007/0288008 A1 | 12/2007 | Park | |
| 2007/0288009 A1 | 12/2007 | Logan | |
| 2007/0288011 A1* | 12/2007 | Logan | A61B 17/7008 606/86 A |
| 2007/0288012 A1 | 12/2007 | Colleran et al. | |
| 2008/0009862 A1 | 1/2008 | Hoffman | |
| 2008/0009864 A1 | 1/2008 | Forton et al. | |

(56) References Cited

U.S. PATENT DOCUMENTS

| | | |
|---|---|---|
| 2008/0015578 A1 | 1/2008 | Erickson et al. |
| 2008/0015579 A1 | 1/2008 | Whipple |
| 2008/0015580 A1 | 1/2008 | Chao |
| 2008/0015584 A1 | 1/2008 | Richelsoph |
| 2008/0015586 A1 | 1/2008 | Krishna et al. |
| 2008/0021454 A1 | 1/2008 | Chao et al. |
| 2008/0021455 A1 | 1/2008 | Chao et al. |
| 2008/0021458 A1 | 1/2008 | Lim |
| 2008/0021459 A1 | 1/2008 | Lim |
| 2008/0021462 A1 | 1/2008 | Trieu |
| 2008/0021464 A1 | 1/2008 | Norin et al. |
| 2008/0021465 A1 | 1/2008 | Shadduck et al. |
| 2008/0021466 A1 | 1/2008 | Shadduck et al. |
| 2008/0021469 A1 | 1/2008 | Holt |
| 2008/0021473 A1 | 1/2008 | Butler et al. |
| 2008/0027432 A1 | 1/2008 | Strauss et al. |
| 2008/0033435 A1 | 2/2008 | Studer et al. |
| 2008/0039838 A1 | 2/2008 | Landry et al. |
| 2008/0039843 A1 | 2/2008 | Abdou |
| 2008/0045951 A1 | 2/2008 | Fanger et al. |
| 2008/0045955 A1 | 2/2008 | Berrevoets et al. |
| 2008/0045957 A1 | 2/2008 | Landry et al. |
| 2008/0051780 A1 | 2/2008 | Vaidya et al. |
| 2008/0051787 A1 | 2/2008 | Remington et al. |
| 2008/0058811 A1 | 3/2008 | Alleyne et al. |
| 2008/0058812 A1 | 3/2008 | Zehnder |
| 2008/0065071 A1 | 3/2008 | Park |
| 2008/0065073 A1 | 3/2008 | Perriello et al. |
| 2008/0065075 A1 | 3/2008 | Dant |
| 2008/0065077 A1 | 3/2008 | Ferree |
| 2008/0065079 A1 | 3/2008 | Bruneau et al. |
| 2008/0071273 A1 | 3/2008 | Hawkes et al. |
| 2008/0071274 A1 | 3/2008 | Ensign |
| 2008/0071277 A1 | 3/2008 | Warnick |
| 2008/0077139 A1 | 3/2008 | Landry et al. |
| 2008/0086125 A1 | 4/2008 | Molz et al. |
| 2008/0086130 A1 | 4/2008 | Lake |
| 2008/0086131 A1 | 4/2008 | Daly et al. |
| 2008/0086132 A1 | 4/2008 | Biedermann et al. |
| 2008/0091214 A1 | 4/2008 | Richelsoph |
| 2008/0097431 A1 | 4/2008 | Vessa |
| 2008/0097434 A1 | 4/2008 | Moumene et al. |
| 2008/0097441 A1 | 4/2008 | Hayes et al. |
| 2008/0097457 A1 | 4/2008 | Warnick |
| 2008/0108992 A1 | 5/2008 | Barry et al. |
| 2008/0119858 A1 | 5/2008 | Potash |
| 2008/0125777 A1 | 5/2008 | Veldman et al. |
| 2008/0125787 A1 | 5/2008 | Doubler et al. |
| 2008/0132952 A1 | 6/2008 | Malandain et al. |
| 2008/0140075 A1 | 6/2008 | Ensign et al. |
| 2008/0140076 A1 | 6/2008 | Jackson |
| 2008/0140133 A1 | 6/2008 | Allard et al. |
| 2008/0147122 A1 | 6/2008 | Jackson |
| 2008/0154307 A1 | 6/2008 | Colleran et al. |
| 2008/0154308 A1 | 6/2008 | Sherman et al. |
| 2008/0161854 A1 | 7/2008 | Bae et al. |
| 2008/0161857 A1 | 7/2008 | Hestad et al. |
| 2008/0161859 A1 | 7/2008 | Nilsson |
| 2008/0161863 A1 | 7/2008 | Arnold et al. |
| 2008/0167687 A1 | 7/2008 | Colleran et al. |
| 2008/0177316 A1 | 7/2008 | Bergeron et al. |
| 2008/0177317 A1 | 7/2008 | Jackson |
| 2008/0177319 A1 | 7/2008 | Schwab |
| 2008/0177321 A1 | 7/2008 | Drewry et al. |
| 2008/0177322 A1 | 7/2008 | Davis et al. |
| 2008/0177327 A1 | 7/2008 | Malandain et al. |
| 2008/0183212 A1 | 7/2008 | Veldman et al. |
| 2008/0183213 A1 | 7/2008 | Veldman et al. |
| 2008/0183215 A1 | 7/2008 | Altarac et al. |
| 2008/0183216 A1 | 7/2008 | Jackson |
| 2008/0183219 A1 | 7/2008 | Jackson |
| 2008/0183223 A1 | 7/2008 | Jeon et al. |
| 2008/0195100 A1 | 8/2008 | Capote et al. |
| 2008/0195153 A1 | 8/2008 | Thompson |
| 2008/0215095 A1 | 9/2008 | Biedermann et al. |
| 2008/0221620 A1 | 9/2008 | Krause |
| 2008/0221692 A1 | 9/2008 | Zucherman et al. |
| 2008/0228227 A1 | 9/2008 | Brown et al. |
| 2008/0228229 A1 | 9/2008 | Walder et al. |
| 2008/0234691 A1 | 9/2008 | Schwab |
| 2008/0234734 A1 | 9/2008 | Walder et al. |
| 2008/0234736 A1 | 9/2008 | Trieu et al. |
| 2008/0234737 A1 | 9/2008 | Boschert |
| 2008/0234739 A1 | 9/2008 | Hudgins et al. |
| 2008/0234744 A1 | 9/2008 | Zylber et al. |
| 2008/0234746 A1 | 9/2008 | Jahng et al. |
| 2008/0243188 A1 | 10/2008 | Walder |
| 2008/0255617 A1 | 10/2008 | Cho et al. |
| 2008/0262546 A1 | 10/2008 | Calvosa et al. |
| 2008/0262548 A1 | 10/2008 | Lange et al. |
| 2008/0262551 A1 | 10/2008 | Rice et al. |
| 2008/0262552 A1 | 10/2008 | Kim |
| 2008/0262553 A1 | 10/2008 | Hawkins et al. |
| 2008/0262554 A1 | 10/2008 | Hayes et al. |
| 2008/0269804 A1 | 10/2008 | Holt |
| 2008/0275504 A1 | 11/2008 | Bonin et al. |
| 2008/0287994 A1 | 11/2008 | Perez-Cruet et al. |
| 2008/0294198 A1 | 11/2008 | Jackson |
| 2008/0300630 A1 | 12/2008 | Bonnema et al. |
| 2008/0300633 A1 | 12/2008 | Jackson |
| 2008/0306528 A1 | 12/2008 | Winslow et al. |
| 2008/0306533 A1 | 12/2008 | Winslow et al. |
| 2008/0306536 A1 | 12/2008 | Frig et al. |
| 2008/0306539 A1 | 12/2008 | Cain et al. |
| 2008/0306540 A1 | 12/2008 | Mitchell et al. |
| 2008/0306543 A1 | 12/2008 | Cain et al. |
| 2008/0306545 A1 | 12/2008 | Winslow |
| 2008/0312694 A1 | 12/2008 | Peterman et al. |
| 2008/0319486 A1 | 12/2008 | Hestad et al. |
| 2009/0005817 A1 | 1/2009 | Friedrich et al. |
| 2009/0012562 A1 | 1/2009 | Hestad et al. |
| 2009/0018583 A1 | 1/2009 | Song et al. |
| 2009/0024165 A1 | 1/2009 | Ferree |
| 2009/0024169 A1 | 1/2009 | Triplett et al. |
| 2009/0030464 A1 | 1/2009 | Hestad et al. |
| 2009/0030465 A1 | 1/2009 | Altarac et al. |
| 2009/0036924 A1 | 2/2009 | Egli et al. |
| 2009/0048631 A1 | 2/2009 | Bhatnagar et al. |
| 2009/0054932 A1 | 2/2009 | Butler et al. |
| 2009/0069849 A1 | 3/2009 | Oh et al. |
| 2009/0082815 A1 | 3/2009 | Zylber et al. |
| 2009/0088799 A1 | 4/2009 | Yeh |
| 2009/0088803 A1 | 4/2009 | Justis et al. |
| 2009/0093820 A1 | 4/2009 | Trieu et al. |
| 2009/0093843 A1 | 4/2009 | Lemoine et al. |
| 2009/0093845 A1 | 4/2009 | Hestad et al. |
| 2009/0093846 A1 | 4/2009 | Hestad et al. |
| 2009/0099606 A1 | 4/2009 | Hestad et al. |
| 2009/0099607 A1 | 4/2009 | Fallin et al. |
| 2009/0099608 A1 | 4/2009 | Szczesny |
| 2009/0105757 A1 | 4/2009 | Gimbel et al. |
| 2009/0105758 A1 | 4/2009 | Gimbel et al. |
| 2009/0105760 A1 | 4/2009 | Frey |
| 2009/0112265 A1 | 4/2009 | Hudgins et al. |
| 2009/0112266 A1 | 4/2009 | Weng et al. |
| 2009/0112267 A1 | 4/2009 | Atkinson et al. |
| 2009/0118767 A1 | 5/2009 | Hestad et al. |
| 2009/0125063 A1 | 5/2009 | Panjabi |
| 2009/0131981 A1 | 5/2009 | White |
| 2009/0138052 A1 | 5/2009 | Biedermann et al. |
| 2009/0149885 A1 | 6/2009 | Durward et al. |
| 2009/0163953 A1 | 6/2009 | Biedermann et al. |
| 2009/0163954 A1 | 6/2009 | Kwak |
| 2009/0163955 A1 | 6/2009 | Moumene et al. |
| 2009/0171395 A1 | 7/2009 | Jeon et al. |
| 2009/0177231 A1 | 7/2009 | Kiester |
| 2009/0177232 A1 | 7/2009 | Kiester |
| 2009/0192548 A1 | 7/2009 | Jeon et al. |
| 2009/0198280 A1 | 8/2009 | Spratt et al. |
| 2009/0198281 A1 | 8/2009 | Rice et al. |
| 2009/0204152 A1 | 8/2009 | Blain |
| 2009/0228045 A1 | 9/2009 | Hayes et al. |
| 2009/0240285 A1 | 9/2009 | Friedrich et al. |
| 2009/0240286 A1 | 9/2009 | Friedrich et al. |

(56) References Cited

U.S. PATENT DOCUMENTS

| | | |
|---|---|---|
| 2009/0240287 A1 | 9/2009 | Cunliffe et al. |
| 2009/0248075 A1 | 10/2009 | Ogilvie et al. |
| 2009/0248077 A1 | 10/2009 | Johns |
| 2009/0248081 A1 | 10/2009 | LeHuec et al. |
| 2009/0248083 A1 | 10/2009 | Patterson et al. |
| 2009/0248088 A1 | 10/2009 | Biedermann |
| 2009/0254123 A1 | 10/2009 | Pafford et al. |
| 2009/0259257 A1 | 10/2009 | Prevost |
| 2009/0259258 A1 | 10/2009 | Perez-Cruet et al. |
| 2009/0270917 A1 | 10/2009 | Boehm |
| 2009/0270920 A1 | 10/2009 | Douget et al. |
| 2009/0270921 A1 | 10/2009 | Krause |
| 2009/0270922 A1 | 10/2009 | Biedermann et al. |
| 2009/0275981 A1 | 11/2009 | Abdelgany et al. |
| 2009/0275983 A1 | 11/2009 | Veldman et al. |
| 2009/0275986 A1 | 11/2009 | Prevost et al. |
| 2009/0281572 A1 | 11/2009 | White |
| 2009/0281573 A1 | 11/2009 | Biedermann et al. |
| 2009/0287250 A1 | 11/2009 | Molz, IV et al. |
| 2009/0287251 A1 | 11/2009 | Bae et al. |
| 2009/0287252 A1 | 11/2009 | Marik et al. |
| 2009/0299411 A1 | 12/2009 | Laskowitz et al. |
| 2009/0318968 A1 | 12/2009 | Duggal et al. |
| 2009/0326582 A1 | 12/2009 | Songer et al. |
| 2009/0326583 A1 | 12/2009 | Moumene et al. |
| 2010/0010542 A1 | 1/2010 | Jackson |
| 2010/0010543 A1 | 1/2010 | Jackson |
| 2010/0010544 A1 | 1/2010 | Fallin et al. |
| 2010/0030271 A1 | 2/2010 | Winslow et al. |
| 2010/0036420 A1 | 2/2010 | Kalfas et al. |
| 2010/0036422 A1 | 2/2010 | Flynn et al. |
| 2010/0036423 A1 | 2/2010 | Hayes et al. |
| 2010/0036424 A1 | 2/2010 | Fielding et al. |
| 2010/0036425 A1 | 2/2010 | Barrus et al. |
| 2010/0042155 A1 | 2/2010 | Biedermann et al. |
| 2010/0042156 A1 | 2/2010 | Harms et al. |
| 2010/0049254 A1 | 2/2010 | Biedermann et al. |
| 2010/0057125 A1 | 3/2010 | Viker |
| 2010/0057126 A1 | 3/2010 | Hestad |
| 2010/0063544 A1 | 3/2010 | Butler |
| 2010/0063545 A1 | 3/2010 | Richelsoph |
| 2010/0063547 A1 | 3/2010 | Morin et al. |
| 2010/0063551 A1 | 3/2010 | Richelsoph |
| 2010/0069964 A1 | 3/2010 | Lechmann |
| 2010/0087858 A1 | 4/2010 | Abdou |
| 2010/0087862 A1 | 4/2010 | Biedermann et al. |
| 2010/0087863 A1 | 4/2010 | Biedermann et al. |
| 2010/0087865 A1 | 4/2010 | Biedermann et al. |
| 2010/0088782 A1 | 4/2010 | Moumene et al. |
| 2010/0094348 A1 | 4/2010 | Biedermann et al. |
| 2010/0137912 A1 | 6/2010 | Alcock et al. |
| 2010/0174319 A1 | 7/2010 | Jackson |
| 2010/0198261 A1 | 8/2010 | Trieu et al. |
| 2010/0198269 A1 | 8/2010 | Taylor et al. |
| 2010/0204736 A1 | 8/2010 | Biedermann et al. |
| 2010/0211104 A1 | 8/2010 | Moumene et al. |
| 2010/0211105 A1 | 8/2010 | Moumene et al. |
| 2010/0222819 A1 | 9/2010 | Timm et al. |
| 2010/0228292 A1 | 9/2010 | Arnold et al. |
| 2010/0249843 A1 | 9/2010 | Wegzyn, III |
| 2010/0256682 A1 | 10/2010 | Fallin et al. |
| 2010/0262187 A1 | 10/2010 | Marik et al. |
| 2010/0262190 A1 | 10/2010 | Ballard et al. |
| 2010/0274285 A1 | 10/2010 | Rouleau |
| 2010/0274287 A1 | 10/2010 | Rouleau et al. |
| 2010/0274288 A1 | 10/2010 | Prevost et al. |
| 2010/0331887 A1 | 12/2010 | Jackson et al. |
| 2011/0301644 A1 | 12/2011 | Belliard |
| 2012/0035660 A1 | 2/2012 | Jackson |
| 2012/0053636 A1 | 3/2012 | Schmocker |
| 2012/0221054 A1 | 8/2012 | Jackson |
| 2013/0123853 A1 | 5/2013 | Seme et al. |
| 2013/0197582 A1 | 8/2013 | Prevost et al. |
| 2014/0018857 A1 | 1/2014 | Jackson |
| 2014/0039555 A1 | 2/2014 | Jackson |
| 2014/0222076 A1 | 8/2014 | Jackson |
| 2014/0343610 A1 | 11/2014 | Jackson |
| 2014/0379030 A1 | 12/2014 | Jackson |
| 2015/0216567 A1 | 8/2015 | Trautwein et al. |
| 2015/0230827 A1 | 8/2015 | Zylber et al. |
| 2015/0320449 A1 | 11/2015 | Jackson |
| 2016/0310169 A1 | 10/2016 | Jackson et al. |
| 2016/0310171 A1 | 10/2016 | Jackson |
| 2016/0346010 A1 | 12/2016 | Jackson |
| 2016/0354118 A1 | 12/2016 | Belliard et al. |
| 2016/0354120 A1 | 12/2016 | Jackson |
| 2017/0100165 A1 | 4/2017 | Jackson |

FOREIGN PATENT DOCUMENTS

| | | |
|---|---|---|
| DE | 4425392 | 11/1995 |
| DE | 19507141 | 9/1996 |
| DE | 19509141 | 9/1996 |
| DE | 19509331 | 9/1996 |
| DE | 29806563 | 7/1998 |
| DE | 29810798 | 12/1999 |
| DE | 19951145 | 5/2001 |
| DE | 10236691 | 2/2004 |
| DE | 102007055745 | 7/2008 |
| EP | 0667127 | 8/1995 |
| EP | 0669109 | 8/1995 |
| EP | 0677277 | 10/1995 |
| EP | 0885598 | 12/1998 |
| EP | 1121902 | 8/2001 |
| EP | 1190678 | 3/2002 |
| EP | 1570795 | 2/2005 |
| EP | 1570795 | 9/2005 |
| EP | 1579816 | 9/2005 |
| EP | 1634537 | 3/2006 |
| FR | 2717370 | 9/1995 |
| FR | 2718946 | 10/1995 |
| FR | 2729291 | 7/1996 |
| FR | 2796545 | 1/2001 |
| FR | 2799949 | 4/2001 |
| FR | 2814936 | 4/2002 |
| FR | 2856578 | 6/2003 |
| FR | 2865373 | 1/2004 |
| FR | 2865375 | 1/2004 |
| FR | 2865377 | 1/2004 |
| FR | 2846223 | 4/2004 |
| FR | 2857850 | 4/2004 |
| FR | 2865378 | 10/2004 |
| GB | 1519139 | 7/1978 |
| GB | 9202745.8 | 4/1992 |
| GB | 2365345 | 2/2002 |
| GB | 2382304 | 5/2003 |
| JP | 10277070 | 10/1998 |
| JP | 2000325358 | 3/2000 |
| SU | 313538 | 10/1971 |
| WO | WO92/03100 | 3/1992 |
| WO | WO94/10927 | 5/1994 |
| WO | WO94/26191 | 11/1994 |
| WO | WO9641582 | 12/1996 |
| WO | WO2001/045576 | 6/2001 |
| WO | WO2001/45576 | 6/2001 |
| WO | WO02/054966 | 7/2002 |
| WO | WO2002/054966 | 7/2002 |
| WO | WO2002/102259 | 12/2002 |
| WO | WO2003/026523 | 4/2003 |
| WO | WO03/068088 | 8/2003 |
| WO | WO2003/068088 | 8/2003 |
| WO | WO2004/041100 | 5/2004 |
| WO | WO2004/075778 | 9/2004 |
| WO | WO2004/089245 | 10/2004 |
| WO | WO2004/107997 | 12/2004 |
| WO | WO2005/000136 | 1/2005 |
| WO | WO2005/000137 | 1/2005 |
| WO | WO2005/020829 | 3/2005 |
| WO | WO2005/065374 | 7/2005 |
| WO | WO2005/065375 | 7/2005 |
| WO | WO2005/072632 | 8/2005 |
| WO | WO2005/082262 | 9/2005 |
| WO | WO2005/099400 | 10/2005 |
| WO | WO2005/104969 | 11/2005 |

(56) References Cited

FOREIGN PATENT DOCUMENTS

| WO | WO2006/012088 | 2/2006 |
|---|---|---|
| WO | WO2006/017616 | 2/2006 |
| WO | WO2006/020530 | 2/2006 |
| WO | WO2006/028537 | 3/2006 |
| WO | WO2006/045094 | 4/2006 |
| WO | WO2006/086537 | 8/2006 |
| WO | WO2006/116662 | 11/2006 |
| WO | WO2006/119241 | 11/2006 |
| WO | WO2007/002409 | 1/2007 |
| WO | WO2007/118045 | 10/2007 |
| WO | WO2007/124222 | 11/2007 |
| WO | WO2007/130835 | 11/2007 |
| WO | WO2007/130840 | 11/2007 |
| WO | WO2007/130941 | 11/2007 |
| WO | WO2008/045210 | 4/2008 |
| WO | WO2008/069420 | 6/2008 |
| WO | WO2008/088990 | 7/2008 |
| WO | WO2008/089075 | 7/2008 |
| WO | WO2008/140756 | 11/2008 |
| WO | WO2005/013839 | 2/2009 |
| WO | WO2009/036541 | 3/2009 |
| WO | WO2010/018316 | 2/2010 |
| WO | WO2010/018317 | 2/2010 |
| WO | WO2010/019704 | 2/2010 |
| WO | WO2010/019857 | 2/2010 |

OTHER PUBLICATIONS

*EBI Omega 21* Brochure, EBI Spine Systems, pub. 1999.
*Claris Instrumentation* Brochure, G Med, pub. 1997.
*VLS System Variable Locking Screw* Brochure, Interpore Cross International, 1999.
*CD Horizon M8 Multi Axial Screw Spinal System* Brochure, Medtronic Sofamor Danek, no publish date.
*Contour Spinal System* Brochure, Ortho Development, no publish date.
*Xia Spinal System* Brochure, Stryker Howmedica Osteonics, no publish date.
*The Rod Plate System* Brochure, Stryker Howmedica Osteonics, pub. Oct. 1999.
*Silhouette Spinal Fixation System* Brochure, Sulzer Medica Spine-Tech, no publish date.
*SDRSW Surgical Dynamics Rod System* Brochure, Surgical Dynamics, pub. 1998-1999.
*Versalok Low Back Fixation System* Brochure, Wright Medical Technology, Inc., pub. 1997.
*The Strength of Innovation* Advertisement, Blackstone Medical Inc., no publish date.
*The Moss Miami 6.0mm System* Advertisement, author unknown, no publish date.
*Spine*, Lipcott, Williams & Wilkins, Inc. vol. 24, No. 15, p. 1495.
Brochure of Tyco/Healthcare/Surgical Dynamics on Spiral Radius 90D, Publication Date: Sep. 2001, pp. 1-8.
Brochure of Sofamor Danek the Spine Specialist, TSRH, Pedicle Screw Spinal System, Publication Date: Jan. 23, 1995.
Brochure of Spinal Concepts, an Abbott Laboratories Company, Pathfinder, Minimally Invasive Pedicle Fixation System, Publication Date: Nov. 2003.
Brochure of Spinal Concepts, InCompass, Thoracolumbar Fixation System, Publication Date: Oct. 2003.
Brochure of Spinal Concepts, Pathfinder, Minimally Invasive Pedicle Fixation System, Publication Date: May 2003.
Brochure of Spinal Concepts, Surgical Technique, InCompass, Thoracolumbar Fixation System, Publication Date: Oct. 2003.
Brochure of Spineline, Current Concepts, Minimally Invasive Posterior Spinal Decompression and Fusion Procedures, Publication Date: Sep./Oct. 2003.
Brochure of Zimmer Spine, Inc., Dynesys® LIS Less Invasive Surgery, The Dynamic Stabilization System, Publication Date: 2005.
Overlap. Merriam-Webster. accessed Apr. 13, 2015 http://www.merriam-webster.com/dictionary/overlap.
U.S. Appl. No. 15/883,794, filed Jan. 30, 2018, Jackson.
U.S. Appl. No. 15/918,181, filed Mar. 12, 2018, Jackson.
U.S. Appl. No. 15/852,866, filed Dec. 22, 2017, Jackson et al.
U.S. Appl. No. 15/835,216, filed Dec. 7, 2017, Jackson et al.
U.S. Appl. No. 15/943,257, filed Apr. 2, 2018, Jackson.

\* cited by examiner

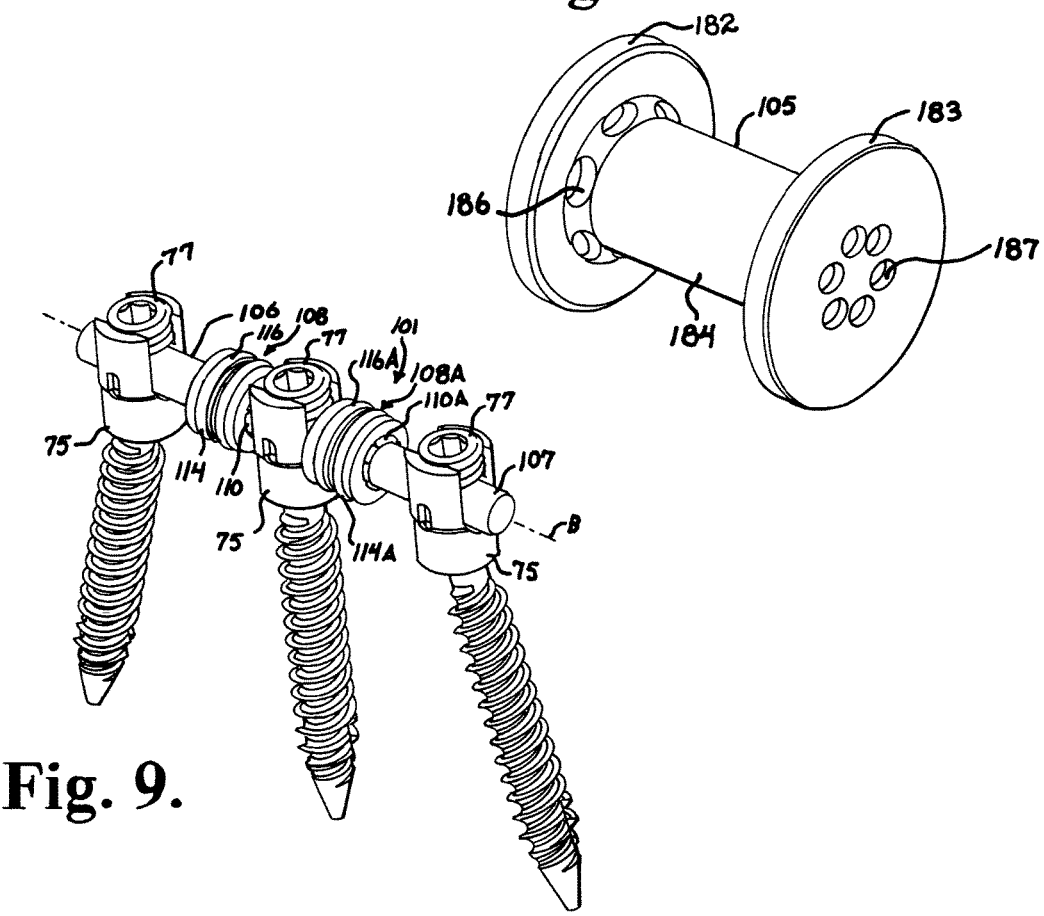
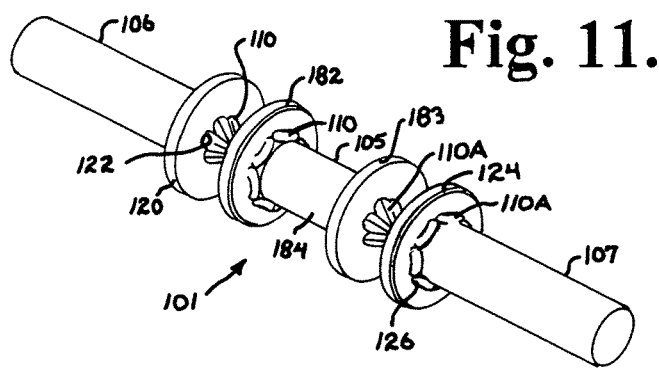

Fig. 12.
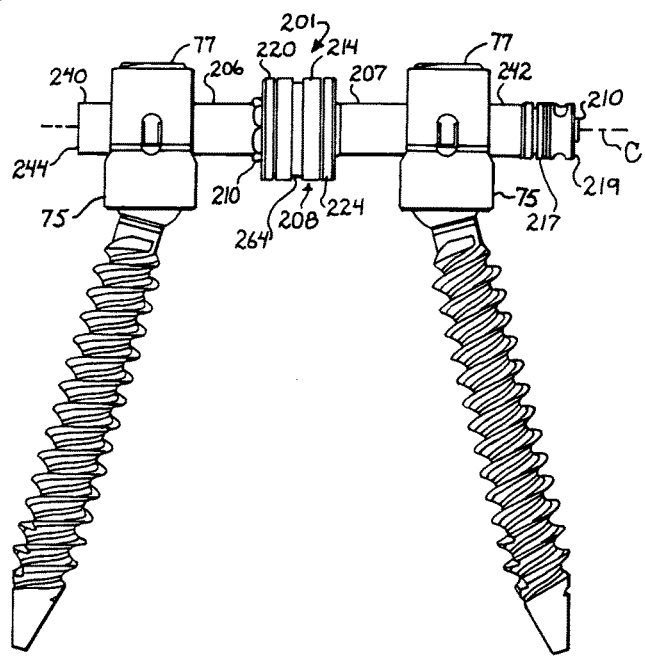
Fig. 13.
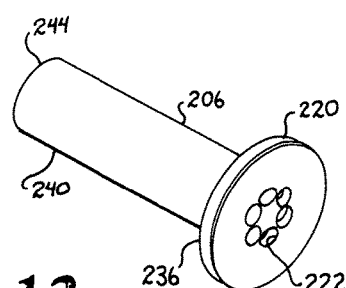
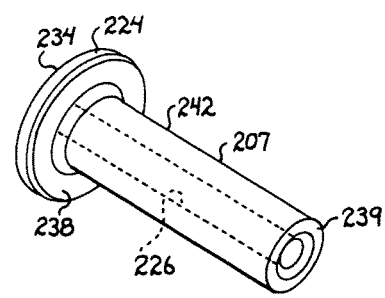
Fig. 14.

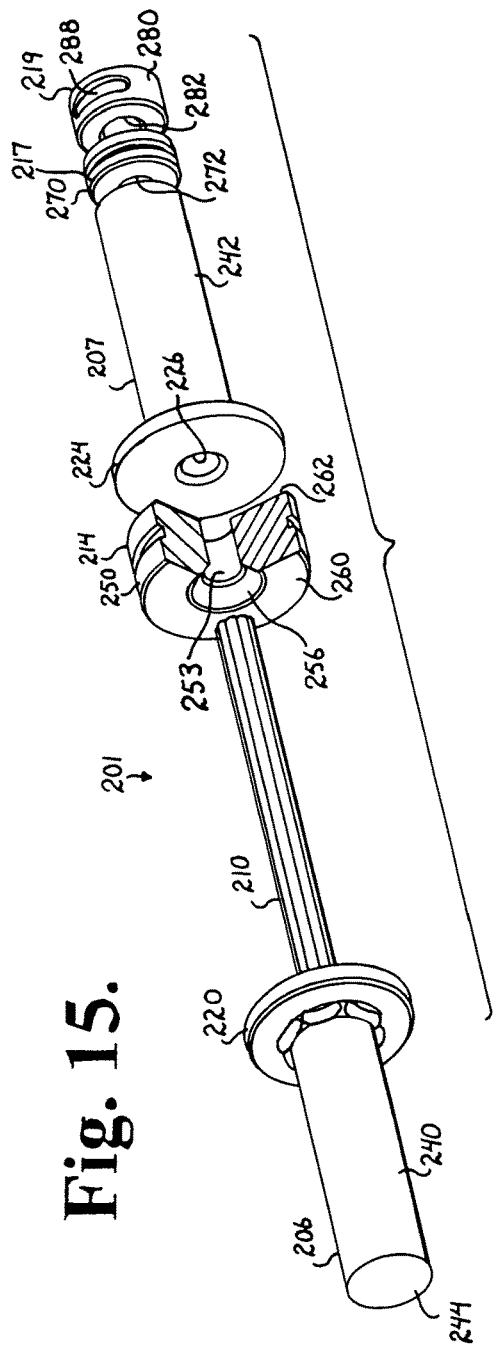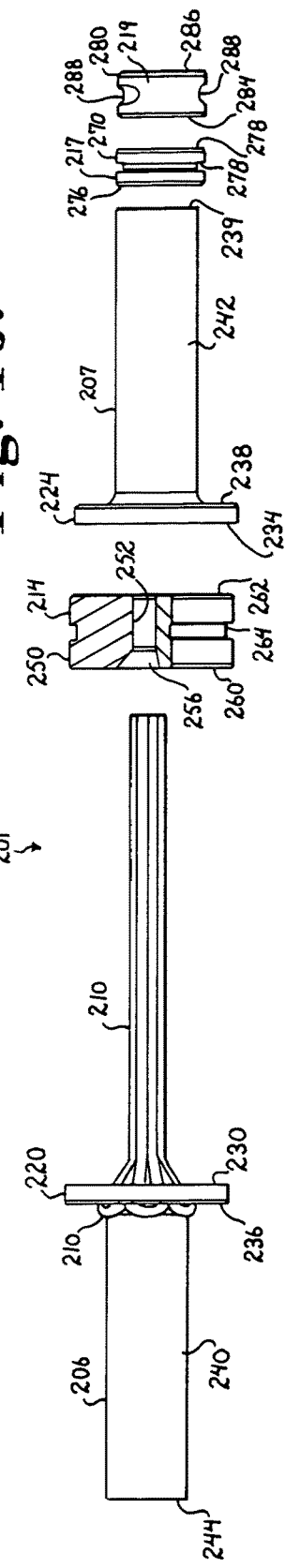

Fig. 20.
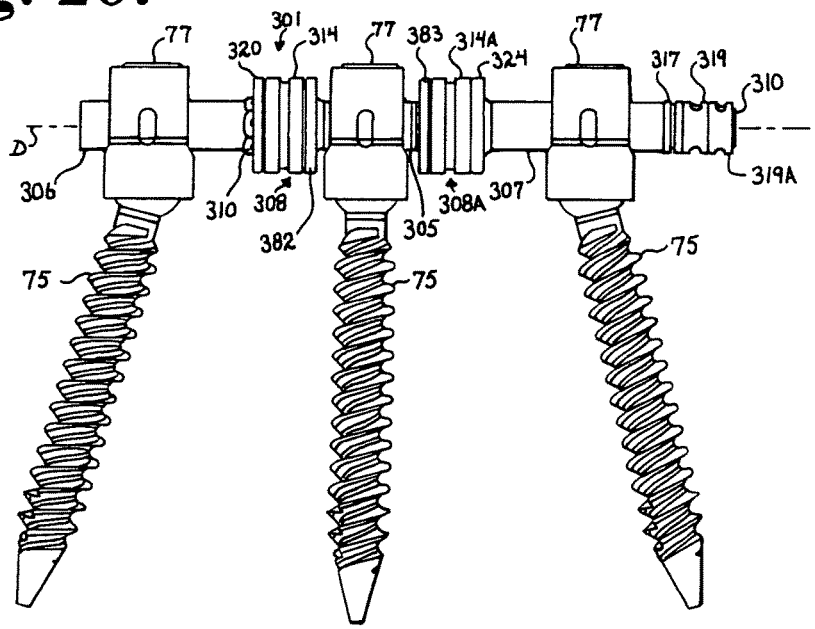
Fig. 21.
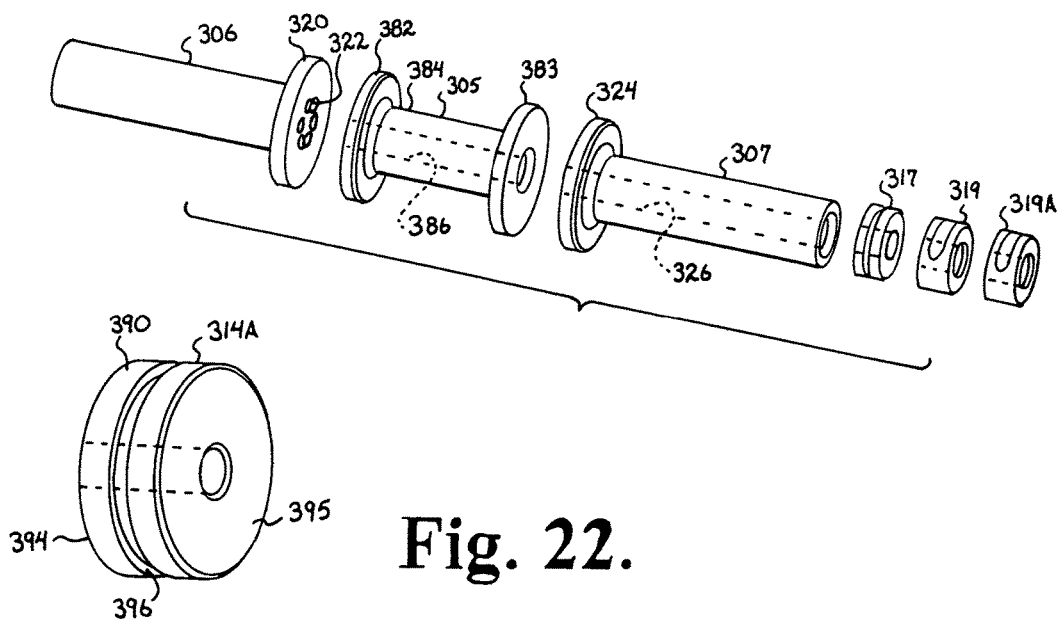
Fig. 22.

ROD-CORD DYNAMIC CONNECTION ASSEMBLIES WITH SLIDABLE BONE ANCHOR ATTACHMENT MEMBERS ALONG THE CORD

CROSS-REFERENCE TO RELATED APPLICATIONS

This application claims the benefit of U.S. Provisional Application No. 60/927,111 filed May 1, 2007, incorporated by reference herein. This application also is a continuation-in-part of U.S. patent application Ser. No. 12/006,460 filed Jan. 3, 2008 that claims the benefit of U.S. Provisional Application No. 60/922,465 filed Apr. 9, 2007; U.S. Provisional Application No. 60/898,870, filed Feb. 1, 2007; and U.S. Provisional Application No. 60/880,969, filed Jan. 18, 2007; all of which are incorporated by reference herein.

BACKGROUND OF THE INVENTION

The present invention is directed to dynamic fixation assemblies for use in bone surgery, particularly spinal surgery, and in particular to longitudinal connecting members for such assemblies, the connecting members being attached to at least two bone fasteners.

Historically, it has been common to fuse adjacent vertebrae that are placed in fixed relation by the installation therealong of bone screws or other bone anchors and cooperating longitudinal connecting members or other elongate members. Fusion results in the permanent immobilization of one or more of the intervertebral joints. Because the anchoring of bone screws, hooks and other types of anchors directly to a vertebra can result in significant forces being placed on the vertebra, and such forces may ultimately result in the loosening of the bone screw or other anchor from the vertebra, fusion allows for the growth and development of a bone counterpart to the longitudinal connecting member that can maintain the spine in the desired position even if the implants ultimately fail or are removed. Because fusion has been a desired component of spinal stabilization procedures, longitudinal connecting members have been designed that are of a material, size and shape to largely resist flexure, extension, torsion, distraction and compression, and thus substantially immobilize the portion of the spine that is to be fused. Thus, longitudinal connecting members are typically uniform along an entire length thereof, and usually made from a single or integral piece of material having a uniform diameter or width of a size to provide substantially rigid support in all planes.

An alternative to fusion, which immobilizes at least a portion of the spine, and the use of more rigid longitudinal connecting members or other rigid structure has been a "soft" or "dynamic" stabilization approach in which a flexible loop-, S—, C- or U-shaped member or a coil-like and/or a spring-like member is utilized as an elastic longitudinal connecting member fixed between a pair of pedicle screws in an attempt to create, as much as possible, a normal loading pattern between the vertebrae in flexion, extension, distraction, compression, side bending and torsion. Another type of soft or dynamic system known in the art includes bone anchors connected by flexible cords or strands, typically made from a plastic material. Such a cord or strand may be threaded through cannulated spacers that are disposed between adjacent bone anchors when such a cord or strand is implanted, tensioned and attached to the bone anchors. The spacers typically span the distance between bone anchors, providing limits on the bending movement of the cord or strand and thus strengthening and supporting the overall system. Such cord or strand-type systems require specialized bone anchors and tooling for tensioning and holding the cord or strand in the bone anchors. Although flexible, the cords or strands utilized in such systems do not allow for elastic distraction of the system once implanted because the cord or strand must be stretched or pulled to maximum tension in order to provide a stable, supportive system.

The complex dynamic conditions associated with spinal movement create challenges for the design of elongate elastic longitudinal connecting members that exhibit an adequate fatigue strength to provide stabilization and protected motion of the spine, without fusion, and that allow for some natural movement of the portion of the spine being reinforced and supported by the elongate elastic or flexible connecting member. A further challenge are situations in which a portion or length of the spine requires a more rigid stabilization, possibly including fusion, while another portion or length may be better supported by a more dynamic system that allows for protective movement.

SUMMARY OF THE INVENTION

Longitudinal connecting member assemblies according to the invention for use between at least two bone anchors provide dynamic, protected motion of the spine and may be extended to provide additional dynamic sections or more rigid support along an adjacent length of the spine, with fusion, if desired. A longitudinal connecting member assembly according to the invention has an inner segment or core made from a cord or cords, the core being fixed at either end to substantially rigid segments, illustrated as rods or tubes, each rod or tubular structure attachable to at least one bone anchor. The core is surrounded by a spacer that is elastomeric. The longitudinal connecting member assembly is dynamically loaded prior to being operatively attached to at least a pair of bone anchors along a patient's spine. The tensioned inner core and the compressed spacer cooperate dynamically, both features having some flexibility in bending, with the outer spacer protecting and limiting flexing movement of the inner core. The spacer may include one or more grooves to aid in compression upon installation between the rigid elongate segments.

In particular, an illustrated inner core of a dynamic longitudinal connecting member according to the invention includes at least one and up to a plurality of tensioned ties, cords or strands surrounded by a compressible outer spacer. At least one end thereof, the cord or cords of the inner core are attached to a plate that is in turn integral with a rigid elongate segment, such as a solid rod or tubular segment. In one embodiment, the inner core includes a plurality of closed loops that are threaded through apertures in a pair of opposed plates, each plate being attached to a longitudinal connecting member, such as a rod segment. The inner core is then pre-tensioned by pulling the plates away from one another and a slitted outer spacer is received over the taunt cords while being compressed and then released between the plates. The plates compress the spacer while placing a distractive force on the cords of the inner core.

In another embodiment, cords are looped through apertures of one plate to attach the inner core to a first elongate member. The cords are also received through a bore of a non-slitted compressible spacer and further through a bore of a second elongate member. The cords are then pulled in a direction away from the plate to place the cords in tension and fixed in place by one or more processes, including placing and depressing a crimping ring at the end of the second elongate member, by directly crimping the second member, and/or by melting the cord or cords, for example. As tension is placed on the cords, the spacer is compressed by rigid plates located on either side thereof.

A variety of embodiments according to the invention are possible. Rods or other substantially rigid structures having different measures of rigidity may be connected according to embodiments of the invention. Either rigid lengths or flexible cords may be of greater or lesser lengths for attaching to one or a plurality of bone anchors.

OBJECTS AND ADVANTAGES OF THE INVENTION

An object of the invention is to provide dynamic medical implant stabilization assemblies having longitudinal connecting members that include both rigid and more flexible sections or lengths, the flexible sections allowing for at least one of bending, torsion, compression and distraction of the assembly. Another object of the invention is to provide such an assembly wherein a portion is pre-tensioned while a cooperating portion is pre-compressed. Another object of the invention is to provide such an assembly wherein the flexible section or sections are insertable into a protective outer sleeve. A further object of the invention is to provide such an assembly wherein the outer sleeve may be compressed upon installation. A further object of the invention is to provide dynamic medical implant longitudinal connecting members that may be utilized with a variety of bone screws, hooks and other bone anchors. Another object of the invention is to provide a more rigid or solid connecting member portion or segment, if desired, such as a solid rod portion integrally linked to one or more flexible portions or segments. Additionally, it is an object of the invention to provide a lightweight, reduced volume, low profile assembly including at least two bone anchors and a longitudinal connecting member therebetween. Furthermore, it is an object of the invention to provide apparatus and methods that are easy to use and especially adapted for the intended use thereof and wherein the apparatus are comparatively inexpensive to make and suitable for use.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 9 is an enlarged perspective view of a second embodiment of a dynamic fixation longitudinal connecting member according to the invention shown with three bone screws.

FIG. 10 is an enlarged perspective view of a rigid rod portion of the connecting member of FIG. 9.

FIG. 11 is an enlarged perspective view of three rigid rod portions and connecting inner core ties of the connecting member of FIG. 9.

FIG. 12 is an enlarged front elevational view of a third embodiment of a dynamic fixation longitudinal connecting member according to the invention including first and second rigid rod portions, an inner core, an outer spacer, an elastic bumper and a crimping ring, and shown attached to a pair of polyaxial bone screws.

FIG. 13 is an enlarged perspective view of the first rigid rod portion of FIG. 12.

FIG. 14 is an enlarged perspective view of the second rigid rod portion of FIG. 12.

FIG. 15 is an enlarged exploded perspective view of the connecting member of FIG. 12, the spacer having a portion broken away to show the detail thereof.

FIG. 16 is an enlarged exploded front elevational view of the connecting member of FIG. 12, the spacer having a portion broken away to show the detail thereof.

FIG. 20 is an enlarged perspective view of a fourth embodiment of a dynamic fixation longitudinal connecting member according to the invention shown with three bone screws.

FIG. 21 is an enlarged exploded perspective view of rigid rod portions, a bumper and a crimping ring of the connecting member of FIG. 20.

FIG. 22 is an enlarged perspective view of one of the spacers of the connecting member of FIG. 20.

DETAILED DESCRIPTION OF THE INVENTION

Figure 1:
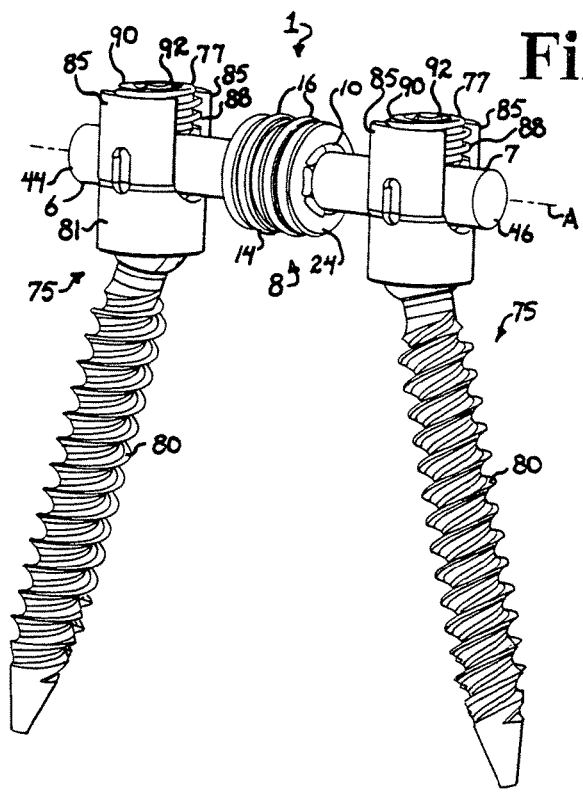
FIG. 1 is an enlarged perspective view of a dynamic fixation longitudinal connecting member according to the invention including first and second rigid rod portions, an inner core, an outer spacer and a pair of support rings, and shown attached to a pair of polyaxial bone screws.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. It is also noted that any reference to the words top, bottom, up and down, and the like, in this application refers to the alignment shown in the various drawings, as well as the normal connotations applied to such devices, and is not intended to restrict positioning of the connecting member assemblies of the application and cooperating bone anchors in actual use.

With reference to FIGS. 1-8, the reference numeral 1 generally designates a non-fusion dynamic stabilization longitudinal connecting member assembly according to the present invention. The connecting member assembly 1 is elongate and substantially cylindrical, having a central axis A. The connecting member assembly 1 generally includes first and second substantially rigid members 6 and 7 with a central, dynamic connection or transition portion or segment, generally 8, disposed therebetween. A tie or a plurality of ties 10 link the rigid members 6 and 7 at the central segment 8. The ties 10 may be any flexible elongate material that fastens, secures or unites the rigid members 6 and 7, including, but not limited to cords, threads, strings, bands, or fibers that may be single or multiple strands, including twisted, braided or plaited materials. The illustrated central segment 8 further includes an outer sleeve or spacer 14 and a pair of support rings 16.

Each of the illustrated rigid members 6 and 7 are substantially cylindrical with one or more circular cross-sections along a length thereof. However, it is foreseen that the members 6 and 7 may have other forms, including but not limited to oval, square and rectangular cross-sections as well as other curved or polygonal shapes. It is foreseen that the member 6 and 7 may be of different materials, different shapes or different sizes, and thus one member may be more rigid or more flexible than the other member. The members 6 and 7 each are of a length for cooperating with at least one and up to a plurality of bone attachment members, such as bone screws or hooks. The member 6 is substantially solid, rigid and cylindrical and further includes a buttress or plate 20 having a plurality of apertures in the form of through bores 22. The member 7 is also substantially solid, rigid and cylindrical and includes a buttress or plate 24 similar or identical to the plate 20. The plate 24 also has a plurality of apertures in the form of through bores 26 running therethrough that are identical or similar to the apertures 22. Each of the bores 22 and 26 extends through the respective plate 20 and 24 at an oblique angle with respect to the axis A. It is foreseen that according to the invention the bores 22 and 26 may also run parallel to the axis A. It is foreseen that the cord, cords, strands or fibers could be embedded into or adhered on the ends of the members 6 and 7.

Figure 2:
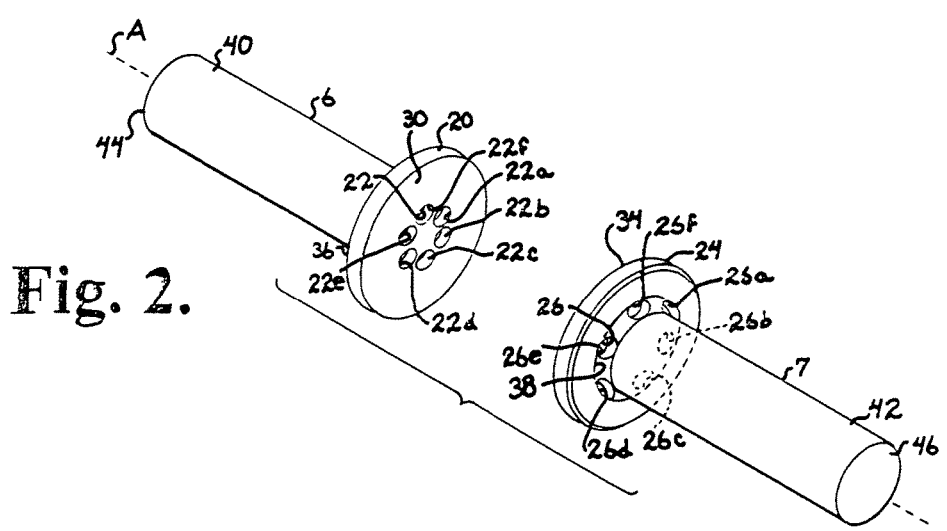
FIG. 2 is an enlarged exploded perspective view of the rigid rod portions of the connecting member of FIG. 1.
Figure 3:
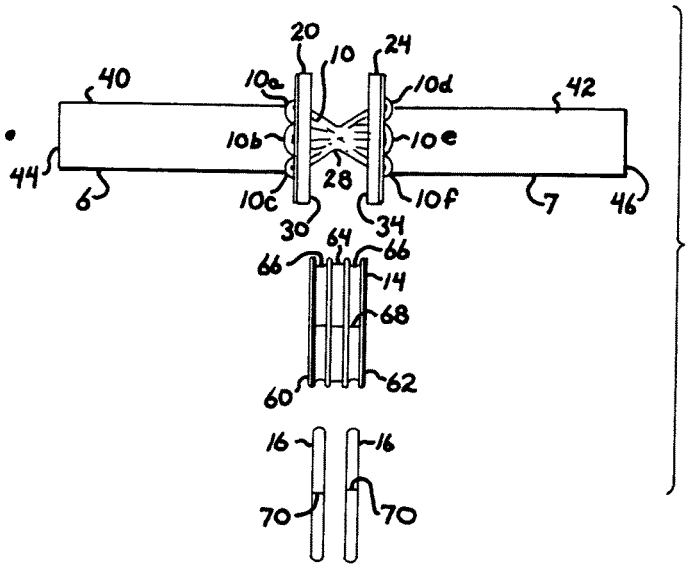
FIG. 3 is an enlarged exploded front elevational view of the connecting member of FIG. 1.
Figure 4:
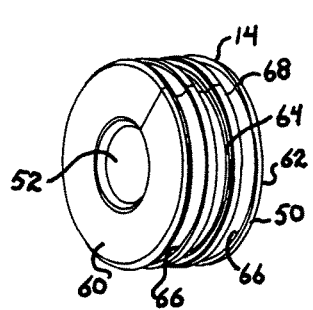
FIG. 4 is an enlarged perspective view of the spacer of FIG. 1.
Figure 5:
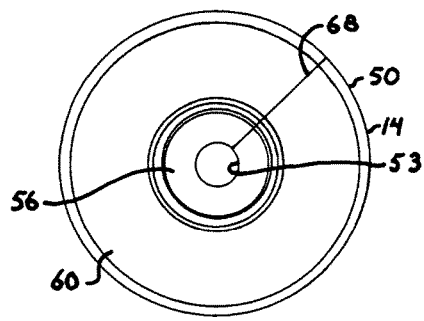
FIG. 5 is an enlarged side elevational view of the spacer of FIG. 1.
Figure 6:
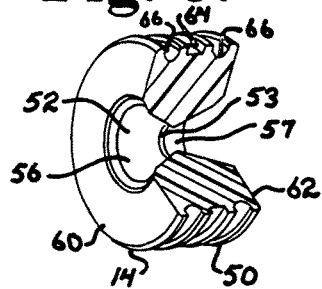
FIG. 6 is an enlarged perspective view of the spacer of FIG. 1 with portions removed to show the detail thereof.

With particular reference to FIG. 2, in the illustrated embodiment, there is shown six bores 22a, 22b, 22c, 22d, 22e and 22f and six cooperating bores 26a, 26b, 26c, 26d, 26e and 26f, each oriented substantially uniformly about the axis A. With reference to both FIGS. 2 and 3, in the illustrated embodiment, the ties 10 are in the form of six independent closed loops, 10a, 10b, 10c, 10d, 10e and 10f, oriented in a crisscross pattern, that attach or tether the rigid members 6 and 7 together at the respective plates 20 and 24. The loops are installed individually, with the individual cords 10 being at least one of knotted, adhered, bonded or melted, to form such a closed loop after threading though two adjacent bores in each of the plates 20 and 24. For example, one looped cord 10 extends through the bores 22a and 22b, looping about the plate 20 at a location between the bores 22a and 22b, and also extends through the bores 26d and 26e, looping about the plate 24 at a location between the bores 26d and 26e. While, in similar fashion, another cord 10 loops about the plate 22 by extending through the bores 22d and 22e and also about the plate 24 by extending through the bores 26a and 26b. As illustrated in FIG. 3, orienting the individual loops 10a-10f in such a crisscross pattern provides a resulting dynamic corded section 8 that slopes or angles inwardly toward the axis A at or near a central location 28 thereof, providing adequate clearance and ready acceptance of the spacer 14 as will be described in greater detail below. It is foreseen that the cords 10 may be individually looped in a configuration substantially parallel to the axis A or a variety of other orientations.

The ties 10 making up the individual or closed loops may be made from a variety of materials, including polyester or other plastic fibers, strands or threads, such as polyethyleneterephthalate. Such cord and cord-like materials usually are placed under axial tension prior to final installation, for example, the loops 10a-10f that are attached to the plates 20 and 24 may be tensioned along the axis A for a selected time prior to installation of the spacer 14 to allow the cords 10 to lengthen and otherwise deform during a primary creep stage. As will be described in more detail below, after the cords 10 reach secondary or steady-state creep, further tension is then placed on the cords 10 in preparation for installation of the spacer 14 between the plates 20 and 24 to ensure dynamic pre-loading of the connector 1, with the corded loops 10a-10f being in tension along the axis A while at the same time the spacer 14 is in compression along the axis A. It is also foreseen that in alternative embodiments of the invention, greater or fewer than six discrete loops or even a single tie 10 may be laced through numerous apertures in the plates 20 and 24 to connect the member 6 to the member 7.

Cords 10 of the invention typically do not illustrate elastic properties, such as any significant additional axial distraction after the assembly 1 is operatively assembled. However, it is foreseen that in some embodiments, the ties or cords 10 may be made of a plastic or rubber (natural or synthetic) having elastic properties, allowing for some further distraction of the central connection portion 8 at the ties 10 during operation thereof.

Figure 8:
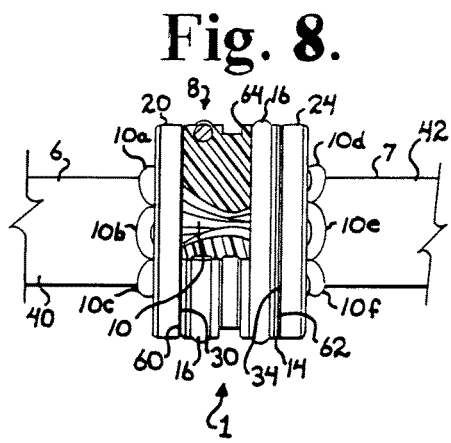
FIG. 8 is an enlarged and partial front elevational view of the connecting member of FIG. 1 with portions broken away to show the detail thereof.

Returning to the longitudinal connecting member rigid members 6 and 7, each of the plates 20 and 24 include respective outer planar surfaces or faces 30 and 34 that operatively face toward one another. Furthermore, each plate 20 and 24 has a respective opposed face 36 and 38. The bores 22a-f open at both the faces 30 and 36 and the bores 26a-f open at both the faces 34 and 38. As illustrated in FIGS. 3 and 8, the cords 10 that form the six discrete closed loops, contact the faces 36 and 38 and attach the plate 20 to the plate 24 with the substantially planar surfaces 30 and 34 facing each other. Extending from the faces 36 and 38 are respective elongate cylindrical portions 40 and 42 of the rigid members 6 and 7. The portion 40 terminates at an end 44 and the portion 42 terminates at an end 46. The portions 40 and 42 are each sized and shaped to attach to at least one bone anchor as will be described in greater detail below. The illustrated portions 40 and 42 are approximately the same size, but it is foreseen that different sizes, lengths and shapes are possible, as well as making the portions 40 and 42 from different materials and also making the plates 20 and 24 from materials that are different than the portions 40 and 42. In the illustrated embodiment, the plates 20 and 24 are integral with respective elongate portions 40 and 42 with the members 6 and 7 being made from metal, metal alloys or other suitable materials, including plastic polymers such as polyetheretherketone (PEEK), ultra-high-molecular weight-polyethylene (UHMWP), polyurethanes and composites, including composites containing carbon fiber.

With particular reference to FIGS. 3-6 and 8, the sleeve or spacer 14 advantageously cooperates with the cords 10 of the central connection or transition portion 8, providing limitation and protection of movement of the cords 10. The spacer 14 also protects patient body tissue from damage that might otherwise occur in the vicinity of the corded central portion 8. The spacer 14 is substantially cylindrical and made from a plastic, such as a thermoplastic elastomer made from a polyurethane or polyurethane blend. The spacer 14 has an external substantially cylindrical outer surface 50 and an internal surface 52 defining a through bore. The internal surface 52 is further defined by a centrally located surface 53 having a circular cross section and a pair of outwardly extending substantially conical surfaces 56 and 57 running from the surface 53 to respective substantially planar end surfaces 60 and 62. When cooperating with the looped cords 10, the end surfaces 60 and 62 are substantially perpendicular to the axis A and the crisscross orientation of the looped cords 10 follow the conical inner surfaces 56 and 57 of the spacer 14 with the central portion 28 of the looped cords being substantially aligned with the inner surface 53. It is foreseen that in some embodiments, the spacer may be of circular, square, rectangular or other cross-section including curved or polygonal shapes. In the illustrated embodiment, the spacer 14 further includes a compression groove 64 and a pair of grooves 66 on either side of the groove 64 sized and shaped to receive the support rings or bands 16. Spacers according to the invention may include one, none or any desired number of grooves. The illustrated grooves 64 and 66 are substantially uniform and circular in cross-section, being formed in the external surface 50 and extending radially toward the internal surface 52. The size of the internal surface 52 allows for some axially directed sliding movement of the spacer 14 with respect to the cords 10 of the section 8. The spacer 14 further includes a radially directed elongate slit or gap opening 68 extending therethrough between the outer surface 50 and the inner surface 52 and through the end surfaces 60 and 62. With reference to FIG. 3, the slit or gap 68 allows for opening the spacer 14 and placing the spacer 14 onto the cords 10 of the section 8 with the gap or slit 68 widening or expanding to receive the cords 10 and then elastically returning the spacer 14 to an original cylindrical shape as shown in FIG. 8, but now positioned with the inner cylindrical surface 52 in sliding, rotating engagement with the cords 10 of the section 8. Also, as shown in FIG. 8, when the spacer 14 is initially placed on the cords 10, the spacer 14 completely surrounds the cords 10 and abuts against the buttress plate surfaces 30 and 34. The cords 10 and cooperating compressible spacer 14 allows for some twist or turn, providing some relief for torsional stresses. The spacer 14, however limits such torsional movement as well as bending movement, providing spinal support, as well as allowing for further compression of the assembly 1 at the transition segment 8. It is noted that in addition to limiting the bendability of the central connection portion 8 and thus providing strength and stability to the assembly 1, the spacer 14 also keeps scar tissue from growing into the portion 8 through the cords 10, thus eliminating the need for a sheath-like structure to be placed, adhered or otherwise applied to the cords 10 on the central connection portion 8. In order to reduce the production of any micro wear debris, that in turn may cause inflammation, the spacer 14 inner surfaces and/or cooperating cord 10 surfaces may be coated with an ultra thin, ultra hard, ultra slick and ultra smooth coating, such as may be obtained from ion bonding techniques and/or other gas or chemical treatments.

Figure 7:
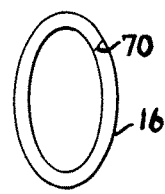
FIG. 7 is an enlarged perspective view of one of the support rings of FIG. 1.

With reference to FIGS. 3 and 7, the support rings or bands 16 are annular and sized and shaped to encircle the spacer 14 and be closely received in the grooves 66. Support rings 16 may be made from a variety of materials, including metals, metal alloys and plastics. A preferred material is tantalum. In the illustrated embodiment, the rings 16 are of circular cross-section and each include a slit or gap 70. The slit or gap 70 allows for opening the ring 16 and placing the ring 16 about the spacer 14 and into one of the grooves 66 with the gap or slit 70 widening or expanding to receive the spacer 14 and then elastically returning the ring 16 to an original circular orientation as shown in FIG. 8, but now positioned about the spacer 14 and within one of the grooves 66. A spot weld, adhesive, or other attachment is then applied to close the slit 70 and secure the ring 16 to itself and about the spacer 14. The pair of rings 16 thus uniformly surround the spacer 14 about the axis A and near each end surface 60 and 62, preventing a gap or gaps from forming at the slit 68. It is foreseen that according to the invention, the support rings or bands may be made of a tough elastic material and therefore not require the slit 70. During installation, the member 6 or 7 would be received by such a band and then the band would be stretched about the spacer 14 and allowed to return to its original form in one of the grooves 66. In a preferred connector 1 of the invention wherein the members 6 and 7 are made from PEEK and cooperate with polyethylene cords 10 and a polyurethane spacer 14, an assembly 1 that is radiolucent results. In such an embodiment, it may be desirable to make the support rings 16 from a metal or metal alloy, such as tantalum, to provide x-ray orientation markers.

The dynamic connecting member assembly 1 cooperates with at least a pair of bone anchors, such as polyaxial bone screws, generally 75, and cooperating closure structures 77 shown in FIG. 1, the assembly 1 being captured and fixed in place at the rigid end portions 40 and 42 by cooperation between the bone screws 75 and the closure structures 77. The dynamic section 8, that is pre-loaded and pre-tensioned, is disposed between the bone screws 75.

It is noted that an advantageous connecting member 1 according to the invention includes a portion 42 made from a metal alloy such as stainless steel that is elongate and intended for fusion along a major portion or section of the spine, for example, the portion 42 may be sized to extend from the sacrum to the thoracic spinal segment T10. Such an elongate portion 42 is thus connectable to a plurality of bone anchors along the spine. Such a connecting member further includes a dynamic section 8, having cords 10 and spacer 14 that is sized for placement, for example, between T9 and T8. Such an embodiment is believed to minimize rapid degeneration and compressive fractures that tend to occur near ends of such elongate connecting member assemblies.

Because the portions 40 and 42 are substantially solid and cylindrical, the connecting member assembly 1 may be used with a wide variety of bone anchors already available for cooperation with rigid rods including fixed, monoaxial bone screws, hinged bone screws, polyaxial bone screws, and bone hooks and the like, with or without compression inserts, that may in turn cooperate with a variety of closure structures having threads, flanges, or other structure for fixing the closure structure to the bone anchor, and may include other features, for example, break-off tops and inner set screws. The bone anchors, closure structures and the connecting member assembly 1 are then operably incorporated in an overall spinal implant system for correcting degenerative conditions, deformities, injuries, or defects to the spinal column of a patient.

The illustrated polyaxial bone screws 75 each include a shank 80 for insertion into a vertebra (not shown), the shank 80 being pivotally attached to an open receiver or head 81. The shank 80 includes a threaded outer surface and may further include a central cannula or through-bore disposed along an axis of rotation of the shank to provide a passage through the shank interior for a length of wire or pin inserted into the vertebra prior to the insertion of the shank 80, the wire or pin providing a guide for insertion of the shank 80 into the vertebra. The receiver 81 has a pair of spaced and generally parallel arms 85 that form an open generally U-shaped channel therebetween that is open at distal ends of the arms 85. The arms 85 each include radially inward or interior surfaces that have a discontinuous guide and advancement structure mateable with cooperating structure on the closure structure 77. The guide and advancement structure may take a variety of forms including a partial helically wound flangeform, a buttress thread, a square thread, a reverse angle thread or other thread like or non-thread like helically wound advancement structure for operably guiding under rotation and advancing the closure structure 77 downward between the receiver arms 85 and having such a nature as to resist splaying of the arms 85 when the closure 77 is advanced into the U-shaped channel. For example, a flange form on the illustrated closure 77 and cooperating structure on the arms 85 is disclosed in Applicant's U.S. Pat. No. 6,726,689, which is incorporated herein by reference.

The shank 80 and the receiver 81 may be attached in a variety of ways. For example, a spline capture connection as described in Applicant's U.S. Pat. No. 6,716,214, and incorporated by reference herein, may be used for the embodiment disclosed herein. Polyaxial bone screws with other types of capture connections may also be used according to the invention, including but not limited to, threaded connections, frictional connections utilizing frusto-conical or polyhedral capture structures, integral top or downloadable shanks, and the like. Also, as indicated above, polyaxial and other bone screws for use with connecting members of the invention may have bone screw shanks that attach directly to the connecting member portion or segment 40 or 42, or may include compression members or inserts that cooperate with the bone screw shank, receiver and closure structure to secure the connecting member assembly 1 to the bone screw and/or fix the bone screw shank at a desired angle with respect to the bone screw receiver that holds the longitudinal connecting member assembly 1. It is foreseen that if the connecting member portions 40 and 42 are fabricated from a plastic such as polyetheretherketone (PEEK), it may be desirable to utilize bone screws that include one or both upper and lower compression inserts that have a saddle or U-shape configuration to closely engage such segments within the bone screw receiver. Although the closure structure 77 of the present invention is illustrated with the polyaxial bone screw 75 having an open receiver or head 81, it is also foreseen that a variety of closure structures may be used in conjunction with any type of medical implant having an open or closed head, including monoaxial bone screws, hinged bone screws, hooks and the like used in spinal surgery.

To provide a biologically active interface with the bone, the threaded shank 80 may be coated, perforated, made porous or otherwise treated. The treatment may include, but is not limited to a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bio-ceramic calcium phosphate coatings include, but are not limited to: alpha-tri-calcium phosphate and beta-tri-calcium phosphate $(Ca_3(PO_4)_2)$, tetra-calcium phosphate $(Ca_4P_2O_9)$, amorphous calcium phosphate and hydroxyapatite $(Ca_{10}(PO_4)_6(OH)_2)$. Coating with hydroxyapatite, for example, is desirable as hydroxyapatite is chemically similar to bone with respect to mineral content and has been identified as being bioactive and thus not only supportive of bone ingrowth, but actively taking part in bone bonding.

With reference to FIG. 1, the closure structure 77 can be any of a variety of different types of closure structures for use in conjunction with the present invention with suitable mating structure on the interior surface of the upstanding arms 85 of the receiver 81. The illustrated closure structure 77 is rotatable between the spaced arms 85, but could be a slide-in closure structure. As described above, the illustrated closure structure 77 is substantially cylindrical and includes an outer helically wound guide and advancement structure in the form of a flange form 88 that operably joins with the guide and advancement structure disposed on the interior of the arms 85. The illustrated closure structure 77 includes a lower or bottom surface that is substantially planar and may include a point and/or a rim protruding therefrom for engaging the portion 40 or 42 outer cylindrical surface. The closure structure 77 has a top surface 90 with an internal drive feature 92, that may be, for example, a star-shaped drive aperture sold under the trademark TORX. A driving tool (not shown) sized and shaped for engagement with the internal drive feature 92 is used for both rotatable engagement and, if needed, disengagement of the closure 77 from the arms 85. The tool engagement structure 92 may take a variety of forms and may include, but is not limited to, a hex shape or other features or apertures, such as slotted, tri-wing, spanner, two or more apertures of various shapes, and the like. It is also foreseen that the closure structure 77 may alternatively include a break-off head designed to allow such a head to break from a base of the closure at a preselected torque, for example, 70 to 140 inch pounds. Such a closure structure would also include a base having an internal drive to be used for closure removal.

In use, at least two bone screws 75 are implanted into vertebrae for use with the longitudinal connecting member assembly 1. Each vertebra may be pre-drilled to minimize stressing the bone. Furthermore, when a cannulated bone screw shank is utilized, each vertebra will have a guide wire or pin (not shown) inserted therein that is shaped for the bone screw cannula of the bone screw shank 80 and provides a guide for the placement and angle of the shank 80 with respect to the cooperating vertebra. A further tap hole may be made and the shank 80 is then driven into the vertebra by rotation of a driving tool (not shown) that engages a driving feature on or near a top portion of the shank 80. It is foreseen that the screws 75 and the longitudinal connecting member assembly 1 can be inserted in a percutaneous or minimally invasive surgical manner.

With particular reference to FIGS. 2, 3 and 8, the longitudinal connecting member assembly 1 is factory assembled to include the looped ties 10 that are initially tensioned to steady state and thereafter further tensioned to receive the spacer 14 that is cut to a desired size so that the spacer 14 is axially compressed between the plates 20 and 24 after insertion of the spacer 14 about the cords or ties 10 and between such plates 20 and 24. In such process, the spacer 14 is opened or expanded at the slit 68 and moved into position over the cords 10 of the central portion 8 and between the plates 20 and 24 and then allowed to elastically return to an original cylindrical form as shown in FIG. 8. The spacer 14 is also axially compressed during insertion such that the spacer 14 easily slides and is received between the surfaces 30 and 34. Thereafter, the rings or bands 16 are expanded at the respective slits 70 and moved into position in the grooves 66, followed by spot welding thereof to result in closed rings 16 encircling the spacer 14. The resulting connecting member assembly 1 is thus dynamically loaded with the cords 10 in tension and the spacer 14 in compression. In some embodiments according to the invention it may be desirable to place one or more pins through the plates 20 and 24 and into the spacer 14 to prevent rotation of the spacer 14 about the axis A relative to the plates 20 and 24. It may also be desirable to use such pins as x-ray markers.

With further reference to FIG. 1, the pre-loaded connecting member assembly 1 is eventually positioned in an open or percutaneous manner in cooperation with the at least two bone screws 75 with the cords 10 and the spacer 14 disposed between and spaced from the two bone screws 75 and with the portions 40 and 42 each being within a U-shaped channel of a cooperating bone screw 75. It is noted that the portions 40 and/or 42 near respective ends 44 and 46 may be selectively trimmed or cut to size before or at the time of surgery, or if longer, attached to the spine with additional bone anchors. Once a desired position is attained, a closure structure 77 is then inserted into and advanced between the arms 85 of each of the bone screws 75. The closure structure 77 is rotated, using a tool (not shown) engaged with the inner drive 92 until a selected pressure is reached at which point the section 40 or 42 is urged toward, but not completely seated in the U-shaped channel of the bone screw 75. For example, about 80 to about 120 inch pounds pressure may be required for fixing the bone screw shank 80 with respect to the receiver 81 at a desired angle of articulation.

The assembly 1 is thus substantially dynamically loaded and oriented relative to the cooperating vertebra, providing relief (e.g., shock absorption) and protected movement with respect to flexion, extension, distraction and compressive forces placed on the assembly 1 and the two connected bone screws 75. The looped cords 10 and the spacer 14 allow for some twisting or turning, providing some relief for torsional stresses. Furthermore, the compressed spacer 14 places some limits on torsional movement as well as bending movement, to provide spinal support. The pre-loaded cords 10 (in tension) and spacer 14 (in compression) allow for compression and some extension of the assembly 1 located between the two bone screws 75, e.g., shock absorption.

If removal of the assembly 1 from any of the bone screw assemblies 75 is necessary, or if it is desired to release the assembly 1 at a particular location, disassembly is accomplished by using the driving tool (not shown) with a driving formation cooperating with the closure structure 77 internal drive 92 to rotate and remove the closure structure 77 from the receiver 81. Disassembly is then accomplished in reverse order to the procedure described previously herein for assembly.

Eventually, if the spine requires more rigid support, the connecting member assembly 1 according to the invention may be removed and replaced with another longitudinal connecting member, such as a solid rod, having the same diameter as the portions 40 and 42, utilizing the same receivers 81 and the same or similar closure structures 77. Alternatively, if less support is eventually required, a less rigid, more flexible assembly, for example, an assembly 1 having portions 40 and 42 made of a more flexible material, but with the same diameter as the rigid portions 40 and 42, may replace the assembly 1, also utilizing the same bone screws 75.

With reference to FIGS. 9-11, an alternative longitudinal connecting member assembly according to the invention, generally 101, has a central axis B and includes rigid members 105, 106 and 107 and first and second dynamic connection portions or sections 108 and 108A. The dynamic sections 108 and 108A include respective closed looped cords 110 and 110A, respective spacers 114 and 114A and respective support rings 116 and 116A. The connecting member assembly 101 provides for two dynamic support sections between a plurality of vertebrae. The illustrated embodiment is shown attached to three bone screws 75 and cooperating closure structures 77 previously described herein. The illustrated rigid members 105, 106 and 107 are each sized for attachment to a single bone anchor or screw. However, it is noted that each such rigid member 105, 106 and 107 may be of greater length (along the axis B) for operative attachment to two or more bone anchors. Furthermore, more than one rigid member 105 may be disposed between rigid members 106 and 107 to provide a plurality of dynamic sections.

The illustrated members 106 and 107 are identical or substantially similar to respective members 6 and 7 previously described herein with respect to the connecting member 1, the member 106 having an end plate 120 and a plurality of bores 122 similar to the plate 20 and bores 22 previously described herein and the member 107 having an end plate 124 and a plurality of bores 126 similar to the plate 24 and bores 26 previously described herein with respect to the member 7. Also, the closed looped cords 110 and 110A are identical or substantially similar to the closed looped cords 10 previously described herein with respect to the connecting member 1 with the cooperating spacers 114 and 114A being identical or substantially similar to the spacer 14 previously described herein with respect to the connecting member 1. Also, the support rings 116 and 116A are identical or substantially similar to the support rings 16 previously described herein with respect to the connecting member 1. However, in the connecting member 101, rather than having closed looped cords that directly attach the members 106 and 107 as previously described with respect to the members 6 and 7, the closed looped cords 110 attach the member 105 with the member 106 and the closed looped cords 110A attach the member 105 with the member 107 in a manner substantially identical to what has been described herein with respect to the close looped cords 10 of the connecting member 1.

Thus, the member 105 may also be considered to be an extender member that is disposed between the members 106 and 107 and is attached to each of such members with the respective closed looped cords 110 and 110A to provide an additional dynamic segment to the assembly 101. The illustrated member 105 includes a pair of opposed end plates 182 and 183 and an integral cylindrical mid-portion 184 extending therebetween. The end plates 182 and 183 are identical or substantially similar to the plates 20 and 24 previously described herein with respect to the members 6 and 7. Thus, the end plates 182 and 183 include respective apertures or through bores 186 and 187 for receiving the respective closed looped cords 110 and 110A. In the illustrated embodiment there are six bores 186 cooperating with the six bores 122 of the member 6 and six bores 187 for cooperating with the six bores 126 of the member 107. The looped cords 110 loop through the bores 122 and the bores 186 while the looped cords 110A loop through the bores 126 and the bores 187. The illustrated cylindrical mid-portion 184 is sized to be received between arms 85 of at least one bone screw 75.

In use, the closed looped cords 110 and 110A are installed in the same manner as previously described herein with respect to the closed looped cords 10 and the spacers 114 and 114A and cooperating support rings 116 and 116A are installed in the same manner as previously described herein with respect to the spacer 14 and the rings 16. Thereafter, the pre-tensioned, pre-compressed connecting member 101 is positioned in an open or percutaneous manner in cooperation with the at least three bone screws 75 with the cords 110 and 110A and cooperating spacers 114 and 114A each disposed between and spaced from such bone screws 75 and portions of the members 105, 106 and 107 each being within a U-shaped channel of a cooperating bone screw 75. A closure structure 77 is then inserted into and advanced between the arms 85 of each of the bone screws 75 to capture and lock the connecting member 101 in a desired location and position along the spine. Disassembly, removal and replacement of the connecting member assembly 101 with a more or less rigid connecting member may be performed in a manner as previously described herein with respect to the connecting member assembly 1.

With reference to FIGS. 12-19, another alternative longitudinal connecting member assembly according to the invention, generally 201 is elongate and substantially cylindrical, having a central axis C. The connecting member assembly 201 generally includes a first rigid anchor member 206 and a second rigid terminal member 207. A central, dynamic connection or transition portion or segment, generally 208, is disposed between the members 206 and 207. A tie, cord or a plurality of ties or cords 210 loop about and through apertures of the anchor member 206 and extend through a bore in the terminal member 207. The ties 210 may be any flexible elongate material that fastens, secures or unites the rigid members 206 and 207, including, but not limited to cords, threads, strings, bands, or fibers that may be single or multiple strands, including twisted, braided or plaited materials. The illustrated central segment 208 further includes a closed, non-slitted outer sleeve or spacer 214. The assembly 201 further includes an elastic bumper 217 and a crimping ring 219.

Each of the illustrated rigid members 206 and 207 are substantially cylindrical with one or more circular cross-sections along a length thereof. However, it is foreseen that the members 206 and 207 may have other forms, including but not limited to oval, square and rectangular cross-sections as well as other curved or polygonal shapes. It is foreseen that the members 206 and 207 may be of different materials, different shapes or different sizes, and thus one member may be more rigid or more flexible than the other member. The members 206 and 207 each are of a length for cooperating with at least one and up to a plurality of bone attachment members, such as bone screws or hooks.

Figure 17:
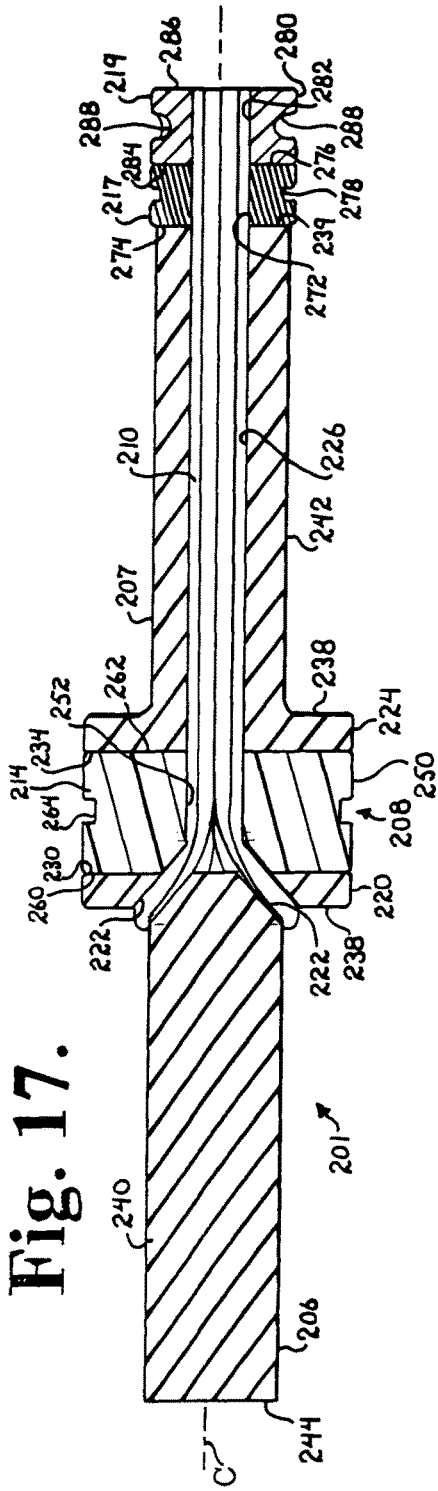
FIG. 17 is an enlarged front elevational view of the connecting member of FIG. 12 with portions broken away to show the detail thereof.
Figure 19:
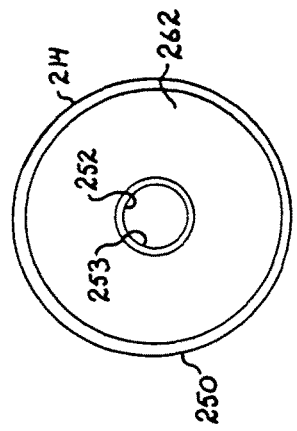
FIG. 19 is an opposed side elevational view of the spacer of FIG. 18.
Figure 18:
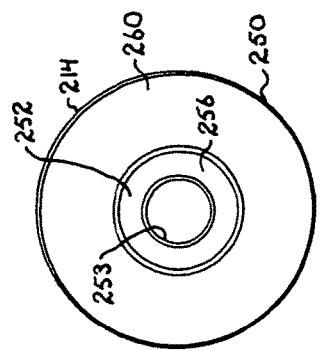
FIG. 18 is an enlarged side elevational view of the spacer shown in FIG. 12.

With particular reference to FIGS. 12, 13 and 17, the anchor member 206 is substantially solid, rigid and cylindrical and further includes a buttress or plate 220 having a plurality of apertures in the form of through bores 222. The member 206 is identical or substantially similar to the member 6 previously described herein with respect to the connecting member assembly 1. The illustrated anchor member 206 has six bores 222 that extend through the plate 220 at an oblique angle with respect to the axis C as best shown in FIG. 17. It is foreseen that according to the invention the bores 222 may also run parallel to the axis C. The ties or cords 210 are in the form of six independent open loops installed individually by looping through pairs of adjacent bores 222 and then extending outwardly away from the plate 220 as shown in FIGS. 15 and 16. Similar to the cords 10 discussed previously herein, the cords 210 are placed under axial tension along the axis C for a selected time prior to final, fixed installation with the other components 214, 207, 217 and 219 to lengthen and otherwise deform the cords 210 during a primary creep stage. After the cords 210 reach secondary or steady-state creep, further tension is then placed on the cords 210 in preparation for final tightening and crimping of the ring 219 as will be described in greater detail below. It is also foreseen that in alternative embodiments of the invention, greater or fewer than six discrete open loops may be laced through apertures in the plate 220 and pulled through the member 207.

The cords 210 of the invention typically do not illustrate elastic properties, such as any significant additional axial distraction after the assembly 201 is operatively assembled. However, it is foreseen that in some embodiments, the ties or cords 210 may be made of a plastic or rubber (natural or synthetic) having elastic properties, allowing for some further distraction of the central connection portion 208 at the ties 210 during operation thereof.

With particular reference to FIG. 14, the terminal member 207 includes a buttress or plate 224 and in inner surface 226 that forms a through bore extending through the entire member 207 in an axial direction, sized and shaped for receiving a length of the bundled cords 210. When operatively connected to the member 206, the bore formed by the inner surface 226 extends along the axis C. With further reference to FIGS. 15-17, each of the plates 220 and 224 include respective outer planar surfaces or faces 230 and 234 that operatively face toward one another. Furthermore, each plate 220 and 224 has a respective opposed face 236 and 238. The bores 222 open at both the faces 230 and 236. The inner surface 226 forming the bore of the member 207 opens at the outer planar surface 234 and also at an end 239. The cords 210 that form the discrete open loops, loop about and contact the face 236, extend along the axis C within the inner surface 226 and extend through the end 239. Extending from and integral to the faces 236 and 238 are respective elongate cylindrical portions 240 and 242 of the respective anchor member 206 and the terminal member 207. The portion 240 terminates at an end 244. The open cords 210 extend completely through the elongate cylindrical portion 242 and into the bumper 217 and the crimping ring 219.

The portions 240 and 242 are each sized and shaped to attach to at least one bone anchor as will be described in greater detail below. The illustrated portions 240 and 242 are approximately the same size and length, but it is foreseen that different sizes, lengths and shapes are possible, as well as making the portions 240 and 242 from different materials and also making the plates 220 and 224 from materials that are different than the portions 240 and 242. In the illustrated embodiment, the plates 220 and 224 are integral with respective elongate portions 240 and 242 with the members 206 and 207 being made from metal, metal alloys or other suitable materials, including plastic polymers such as polyetheretherketone (PEEK), ultra-high-molecular weight-polyethylene (UHMWP), polyurethanes and composites, including composites containing carbon fiber.

With particular reference to FIGS. 15-19, the sleeve or spacer 214 advantageously cooperates with the cords 210 of the central connection or transition portion 208, providing limitation and protection of movement of the cords 210. The spacer 214 also protects patient body tissue from damage that might otherwise occur in the vicinity of the corded central portion 208. The spacer 214 is substantially cylindrical and made from a plastic, such as a thermoplastic elastomer made from a polyurethane or polyurethane blend.

The spacer 214 has an external substantially cylindrical outer surface 250 and an internal surface 252 defining a through bore. The internal surface 252 is further defined by a substantially cylindrical surface 253 having a circular cross section and an outwardly extending substantially conical surface 256 running from the surface 253 to a substantially planar end surface 260. The spacer 214 further includes an opposed planar end surface 262. The inner cylindrical surface 253 opens to the end surface 262.

When operatively cooperating with the looped cords 210, the end surfaces 260 and 262 of the spacer 214 are substantially perpendicular to the axis C. Also, when installed within the inner cylindrical surface 226, the cords 210 are drawn inwardly from the bores 222 and toward the axis C. The conical inner surface 256 of the spacer 214 provides clearance for the cords 210 at the plate surface 230 while the cylindrical inner surface 253 aligns the cords 210 with the inner bore formed by the inner surface 226 of the terminal member 207. It is also foreseen that the cords 210 may be twisted or otherwise connected to form a substantially cylindrical unit prior to insertion in the spacer 214 and the terminal member 207. It is foreseen that in some embodiments, the spacer 214 may be of circular, square, rectangular or other cross-section including curved or polygonal shapes. In the illustrated embodiment, the spacer 214 further includes a compression groove 264. Spacers according to the invention may include one, none or any desired number of grooves. The illustrated groove 264 is substantially uniform and circular in cross-section, being formed in the external surface 250 and extending radially toward the internal surface 252. The size of the internal surface 252 allows for some axially directed sliding movement of the spacer 214 with respect to the cords 210. The cords 210 and cooperating compressible spacer 214 allow for some twist or turn, providing some relief for torsional stresses. The spacer 214, however limits such torsional movement as well as bending movement, providing spinal support, as well as allowing for further compression of the assembly 1 at the flexible central connection portion 208. It is noted that in addition to limiting the bendability of the central connection portion 208 and thus providing strength and stability to the assembly 201, the spacer 214 also keeps scar tissue from growing into the portion 208 through the cords 210, thus eliminating the need for a sheath-like structure to be placed, adhered or otherwise applied to the cords 210 on the central connection portion 208. In order to reduce the production of micro wear debris, that in turn may cause inflammation, the spacer 214 inner surfaces and/or cooperating cord 210 surfaces may be coated with an ultra thin, ultra hard, ultra slick and ultra smooth coating, such as may be obtained from ion bonding techniques and/or other gas or chemical treatments.

With particular reference to FIGS. 15 to 17, the bumper 217 is substantially cylindrical, including an outer surface 270 and an inner surface 272 forming a substantially cylindrical through bore that opens at planar end surfaces 274 and 276 and operatively extends along the axis C. The bumper 217 further includes a compression groove 278 that is similar in form and function to the compression groove 264 of the spacer 214. The bumper 217 is sized and shaped to receive the elongate cords 210 through the inner surface 272. The bumper 217 is preferably made from an elastomeric material such as polyurethane. The bumper 217 provides axial elastic distraction of the cords 210 as will be described in greater detail below.

Also with reference to FIGS. 15 to 17, the crimping ring 219 is substantially cylindrical and includes an outer surface 280 and an inner surface 282 forming a substantially cylindrical through bore that opens at planar end surfaces 284 and 286 and operatively extends along the axis C. The crimping ring 219 is sized and shaped to receive the elongate cords 210 through the inner surface 282. The crimping ring 219 further includes a pair of crimp or compression grooves 288 that are pressable and deformable inwardly toward the axis C upon final tensioning of the cords 210 during assembly of the connector 201 to engage and hold the cords 210 in tension and thereby transmit compressive force to the elastic spacer 214. The crimping ring 219 is preferably made from a stiff, but deformable material, including metals and metal alloys. As will be discussed with respect to a further embodiment of the invention described below, the cords 210 may be threaded through two crimping rings 219 placed adjacent to one another, with a preliminary crimping ring being at a terminal end of the assembly 201. Such a preliminary ring is crimped to initially lock the assembly together with the cords 210 in tension. If further creep and deformation of the cords 210 decreases the axial tension on the cords 210 within the assembly 201, the cords 210 may be re-tensioned and locked into place with the second or final crimping ring. The preliminary crimping ring may then be sliced off of the assembly 201 and discarded.

With reference to FIG. 12, the dynamic connecting member assembly 201 cooperates with at least a pair of bone anchors, such as the polyaxial bone screws, generally 75, and cooperating closure structures 77 described previously herein, the assembly 201 being captured and fixed in place at the rigid portions 240 and 242 by cooperation between the bone screws 75 and the closure structures 77. The dynamic section 208, that is pre-loaded and pre-tensioned, is disposed between the bone screws 75.

With particular reference to FIGS. 12 and 15-17, the longitudinal connecting member assembly 201 is factory assembled by looping six ties 210 about and through the bores 222 of the plate 220 of the anchor member 207 to form the twelve strands or cords 210 that are then threaded through the remaining components of the assembly 201. It is noted that the ties 210 may be initially tensioned to steady state and thereafter further tensioned after assembly with the other components. Alternatively, the twelve cords or strands 210 that are anchored to the member 206 are initially passed through the spacer 214 inner surface 252, followed by the terminal member 207 internal surface 226, then the bumper 217 inner surface 272 and finally the crimping ring 219 inner surface 282 and out the end 286. Thereafter, the spacer 214, the terminal member 207, the bumper 217 and the crimping ring 219 are snugged up against the plate 220 of the anchor member 206 and tension is applied to the bundle of twelve cords 210. Tension is increased on the cord bundle 210 until the elastic spacer and the elastic bumper 217 are compressed and the cords have stopped stretching. Thereafter, the crimping ring is crimped using a tool (not shown) that presses on the opposed grooves 288 and deforms toward the axis C to make contact and firmly grip the cords 210, keeping the cords 210 in the desired tension and locking the components of the assembly 201 in place. The resulting connecting member assembly 201 is thus dynamically loaded with the cords 210 in tension and the spacer 214 and elastic bumper 217 in compression. In some embodiments according to the invention it may be desirable to place one or more pins through the plates 220 and 224 and into the spacer 214 to prevent rotation of the spacer 214 about the axis C relative to the plates 220 and 224. It may also be desirable to use such pins as x-ray markers.

With further reference to FIG. 12, the pre-loaded connecting member assembly 201 is eventually positioned in an open or percutaneous manner in cooperation with the at least two bone screws 75 with the spacer 214 disposed between and spaced from the two bone screws 75 and with the portions 240 and 242 each being within a U-shaped channel of a cooperating bone screw 75. A closure structure 77 is then inserted into and advanced between the arms 85 of each of the bone screws 75. The closure structure 77 is rotated, using a tool (not shown) engaged with the inner drive 92 until a selected pressure is reached at which point the section 240 or 242 is urged toward, but not completely seated in the U-shaped channel of the bone screw 75. For example, about 80 to about 120 inch pounds pressure may be required for fixing the bone screw shank 80 with respect to the receiver 81 at a desired angle of articulation.

The assembly 201 is thus substantially dynamically loaded and oriented relative to the cooperating vertebra, providing relief (e.g., shock absorption) and protected movement with respect to flexion, extension, distraction and compressive forces placed on the assembly 201 and the two connected bone screws 75. The looped cords 210 and the spacer 214 allow for some twisting or turning, providing some relief for torsional stresses. Furthermore, the compressed spacer 214 places some limits on torsional movement as well as bending movement, to provide spinal support. The pre-loaded cords 210 (in tension) and spacer 214 (in compression) allow for compression and some extension of the assembly 201 located between the two bone screws 75, e.g., shock absorption. Disassembly, removal and replacement of the connecting member assembly 201 with a more or less rigid connecting member may be performed in a manner as previously described herein with respect to the connecting member assembly 1.

With reference to FIGS. 20-22, another longitudinal connecting member assembly according to the invention, generally 301, has a central axis D and includes an intermediate rigid member 305, a rigid anchor member 306, a rigid terminal member 307 and first and second dynamic connection portions or sections 308 and 308A. An open loop cord bundle 310 extends through both the sections 308 and 308A. The dynamic sections 308 and 308A further include respective spacers 314 and 314A. The connecting member assembly 301 provides for two dynamic support sections between a plurality of vertebrae. The illustrated embodiment is shown attached to three bone screws 75 and cooperating closure structures 77 previously described herein. The illustrated rigid members 305, 306 and 307 are each sized for attachment to a single bone anchor or screw. However, it is noted that each such rigid member 305, 306 and 307 may be of greater length (along the axis D) for operative attachment to two or more bone anchors. Furthermore, more than one rigid member 305 may be disposed between rigid members 306 and 307 to provide a plurality of dynamic sections.

The connecting member assembly 301 is substantially similar to the connecting member assembly 201 previously described herein with the exception of three components: the additional intermediate rigid member 305, the additional spacer 314A and the additional crimping ring 319A. The illustrated members 306 and 307 are identical or substantially similar to respective members 206 and 207 previously described herein with respect to the connecting member 201, the member 306 having an end plate 320 and a plurality of bores 322 similar to the plate 220 and bores 222 previously described herein and the member 307 having an end plate 324 and a through bore 326 similar to the plate 224 and bore 226 previously described herein with respect to the member 207. Also, the open looped cord bundle 310 is identical or substantially similar to the open looped cord bundle 210, with the exception that the bundle 310 is of greater axial length (along the axis D) as compared to the corded bundle 210 previously described herein with respect to the connecting member 201. The spacer 314 that is disposed between the member 306 and the member 305 is identical or substantially similar to the spacer 214 previously described herein with respect to the connecting member 201. Also, the elastic bumper 317 and both crimping rings 319 and 319A are identical or substantially similar to the respective bumper 217 and crimping ring 219 previously described herein with respect to the connecting member 201.

With particular reference to FIGS. 20 and 21, the intermediate rigid member 305 is disposed between the members 306 and 307 and provides for an additional dynamic connection section 308A. In particular, the member 301 includes a pair of opposed end plates 382 and 383 and an integral cylindrical mid-portion 384 that extends therebetween. The end plates 382 and 383 are identical or substantially similar to the plate 324 of the member 307. The member 305 further includes a through bore 386 running through the entire member 305, from the end plate 382 to the end plate 383 and axially centrally through the cylindrical mid-portion 384. The illustrated cylindrical mid-portion 384 is sized to be received between arms 85 of at least one bone screw 75.

The spacer 314 receives the cord bundle 310 at a location between the plate 320 of the anchor member 306 and the plate 382 of the intermediate rigid member 305. The spacer 314A receives the cord bundle 310 at a location between the plate 383 of the member 305 and the plate 324 of the terminal member 307. The illustrated spacer 314A is substantially similar to the spacer 314 and the spacer 214 previously described herein with respect to the connecting member assembly 201, having an outer cylindrical surface 390, an inner surface 392 defining a through bore running between planar surfaces 394 and 395 and at least one outer compression groove 396. However, unlike the spacers 214 and 314, the inner surface 392 of the spacer 314A is cylindrical and defines a bore of constant circular cross-section sized and shaped to receive a length of the cord bundle 310.

In use, the open looped cord bundle 310 is installed on the anchor member 306 by looping through the apertures 322 in the same manner as previously described herein with respect to the installation of the open looped cord bundle 210 through the apertures 222. The twelve cords or strands 310 that are anchored to the member 306 are initially passed through the bore in the spacer 314, followed by the bore formed by the intermediate member 305 internal cylindrical surface 386, then the bore formed by the spacer 314A internal surface 392, followed by the bore formed by the terminal member 307 internal surface 326, then the bore of the bumper 317, the bore of the crimping ring 319 and finally through the bore of the crimping ring 319A. Thereafter, the spacer 314, the intermediate member 305, the spacer 314A, the terminal member 307, the bumper 317, the crimping ring 319 and the crimping ring 319A are snugged up against the plate 320 of the anchor member 306 and tension is applied to the bundle of twelve cords 310. Tension is increased on the cord bundle 310 until the elastic spacers 314 and 314A and the elastic bumper 317 are compressed and the cords 310 have stopped stretching. Thereafter, the end crimping ring 319A is crimped using a tool (not shown) that presses on opposed grooves of the ring 319A and deforms the ring toward the axis D to make contact and firmly grip the cords 310. If viscoelastic changes decrease the axial tension in the cord bundle 310, the assembly 301 may be re-tensioned by pulling the cords 310 away from the anchor member 306 until a desired tension is again reached. At that time, the other crimping ring 319 is crimped using a tool (not shown) that presses on opposed grooves of the ring 319 and deforms the ring toward the axis D to make contact and firmly grip the cords 310. Thereafter, the crimping ring 319A is sliced off of the assembly 301. The resulting connecting member assembly 301 is thus dynamically loaded with the cords 310 in tension with the spacers 314 and 314A and the elastic bumper 317 in compression.

With further reference to FIG. 20, the pre-loaded connecting member assembly 301 is eventually positioned in an open or percutaneous manner in cooperation with the at least three bone screws 75 with the spacers 314 and 314A disposed between and spaced from the bone screws 75 and with cylindrical portions of each of the members 305, 306 and 307 being within a U-shaped channel of a cooperating bone screw 75. A closure structure 77 is then inserted into and advanced between the arms 85 of each of the bone screws 75. The closure structure 77 is rotated, using a tool (not shown) engaged with the inner drive 92 until a selected pressure is reached, for example, about 80 to about 120 inch pounds pressure may be required for fixing the bone screw shank 80 with respect to the receiver 81 at a desired angle of articulation.

The assembly 301 is thus substantially dynamically loaded and oriented relative to the cooperating vertebra, providing relief (e.g., shock absorption) and protected movement with respect to flexion, extension, distraction and compressive forces placed on the assembly 301 and the three connected bone screws 75. The cords 310 and the spacers 314 and 314A allow for some twisting or turning, providing some relief for torsional stresses. Furthermore, the compressed spacers 314 and 314A place some limits on torsional movement as well as bending movement, to provide spinal support. The pre-loaded cords 310 (in tension) and spacers 314 and 314A (in compression) allow for compression and some extension of the assembly 301 located between the two bone screws 75, e.g., shock absorption. Disassembly, removal and replacement of the connecting member assembly 301 with a more or less rigid connecting member may be performed in a manner as previously described herein with respect to the connecting member assembly 1.

It is to be understood that while certain forms of the present invention have been illustrated and described herein, it is not to be limited to the specific forms or arrangement of parts described and shown.

What is claimed and desired to be secured by Letters Patent is as follows:

1. A medical implant assembly comprising a bone anchor and a pivotal bone screw, the bone anchor and pivotal bone screw cooperating with a longitudinal connecting member, wherein the longitudinal connecting member comprises:
    a) a substantially solid first connecting member having a length with a portion for attachment to the bone anchor, the first connecting member including a first end portion thereof connected to a first end portion of a tensionable cord;
    b) a second connecting member having a portion for attachment to the pivotal bone screw, the second connecting member including an internal opening along an entire length thereof, the cord positioned within and extending entirely through the internal opening, the second connecting member being in slidable relation with the cord before and after the cord is tensioned;
    c) an outer spacer located between the bone anchor and the pivotal bone screw and surrounding the cord and being in slidable relation therewith;
    d) a multi-part stiff end structure having a plurality of parts, each part being engaged with and compressively securable against the cord to hold the cord in tension, such that the plurality of parts no longer have a slidable relationship with respect to the cord, the multi-part stiff end structure comprising a non-threaded through-bore for slidably receiving a second end portion of the cord therethrough prior to tensioning of the cord along the second end portion with a tool; and
    e) an elastically compressible bumper having a through-bore, the cord extending through the bumper through-bore, the bumper located between the second connecting member and the multi-part stiff end structure, the bumper initially being in slidable engagement with the cord, and wherein the multi-part stiff end structure is only secured to the cord after the cord is tensioned along the second end portion of the cord.

2. The assembly of claim 1, wherein the second connecting member portion is substantially rigid.

3. The assembly of claim 1, wherein the outer spacer is in compression.

4. The assembly of claim 1, wherein the first connecting member has an integral plate.

5. The assembly of claim 1, wherein the multi-part stiff end structure includes two separate parts with surfaces engageable with each other, the engagement surfaces being non-tapered.

6. The assembly of claim 1, wherein the first end portion of the tensionable cord is connected to the first connecting member at a location substantially outside of a head of the bone anchor.

7. The assembly of claim 1, wherein the multi-part stiff end structure includes a closed circumferentially extending inner surface at least a portion of which compressively and fixedly engages the cord after the cord is tensioned.

8. The assembly of claim 1, wherein the multi-part stiff end structure has a pair of opposed crimping surfaces to compressively and fixedly engage the cord after the cord is tensioned.

9. The assembly of claim 1, wherein the multi-part stiff end structure includes a closed crimping ring.

10. The assembly of claim 1, wherein the multi-part stiff end structure is positioned and secured on the cord entirely outside of the bumper.

11. The assembly of claim 1, wherein the cord cooperates with one of the bone anchor or the pivotable bone screw in a fixed relation to provide continuous tension in the cord, and wherein the one of the bone anchor or the pivotable bone screw is in slidable relation with the cord after the cord is tensioned and the multi-part stiff end structure is compressively secured thereto.

12. The assembly of claim 1, wherein the cord is re-tensionable after the cord has been tensioned.

13. The assembly of claim 1, further comprising:
    a bone anchor receiver coupled to the first connecting member, the cord positioned entirely outside of the bone anchor receiver.

14. The assembly of claim 1, wherein the cord is tensioned before the longitudinal connecting member is attached to the bone anchor and the pivotal bone screw.

15. The assembly of claim 1, wherein the cord is tensioned after the first and second connecting members are attached to the bone anchor and the pivotal bone screw, respectively.

16. The assembly of claim 1, wherein the second connecting member has an integral plate.

17. The assembly of claim 1, wherein the multi-part stiff end structure compressive securement against the cord is devoid of cord internal penetration.

18. The assembly of claim 1, wherein the cord is tensionable from only the end on which the multi-part stiff end structure is secured.

19. The assembly of claim 1, wherein the spacer and the bumper are spaced apart from the bone anchor and the pivotal bone screw when the cord is tensioned.

20. The assembly of claim 1, wherein the spacer is elastically compressible.

21. The assembly of claim 1, wherein the first connecting member portion for attachment to the pivotal bone screw has a cylindrical outer surface.

22. A medical implant assembly comprising first and second bone anchors, the first and second bone anchors cooperating with a longitudinal connecting member, wherein the longitudinal connecting member comprises:
   a) a first connecting member portion attachable to the first bone anchor, the first connecting member portion having a closed internal opening along an entire length thereof, the connecting member portion positionable within and securable to the first bone anchor;
   b) a tensionable cord positioned within and extending entirely through the internal opening and tensioned to a stable length, the first bone anchor being in slidable relation with respect to the cord before and after tensioning; and
   c) a multi-part stiff end structure having a plurality of parts each engageable with and compressively securable against the cord so as the to hold the cord in tension, the multi-part stiff end structure comprising a non-threaded interior surface extending entirely through the stiff end structure for slidably receiving the cord therethrough prior to tensioning.

23. The assembly of claim 22, wherein the first bone anchor is a first polyaxial bone screw.

24. The assembly of claim 22, wherein the longitudinal connecting member further comprises an outer spacer being located between the first bone anchor and the second bone anchor and surrounding the cord in slidable relation therewith.

25. The assembly of claim 22, wherein the longitudinal connecting member further comprises an elastically compressible bumper having a through-bore, the cord extending through the bumper through-bore, the bumper located between the second bone anchor and the multi-part stiff end structure, and the bumper being in slidable engagement with the cord.

26. The assembly of claim 22, wherein the second bone anchor is a second polyaxial bone screw.

27. The assembly of claim 26, wherein the second polyaxial bone screw further comprises a compression insert, such that the compression insert cooperates in locking the second polyaxial bone screw.

28. The assembly of claim 22, wherein the multi-part stiff end structure is at least partially releaseable with respect to the cord to allow the medical implant assembly to be further tensioned.

29. The assembly of claim 22, wherein the multi-part stiff end structure is secured to the cord only after the cord has been tensioned.

30. The assembly of claim 22, wherein the first connecting member is attached to a first bone anchor receiver.

31. The assembly of claim 30, wherein the first connecting member has an outer cylindrical surface.

32. The assembly of claim 22, wherein the cord is tensioned to a stable length prior to the longitudinal connecting member being attached to the first and second bone anchors.

33. The assembly of claim 22, wherein the cord is connected to the second bone anchor.

34. A medical implant assembly comprising first and second bone anchors cooperating with a longitudinal connecting member, wherein the longitudinal connecting member comprises:
   a) a first connecting member having an elongated stiff portion for being fixedly attachable to the first bone anchor, the first connecting member including a first end portion connected to a cord portion tensionable to a length;
   b) a second connecting member having a portion for being fixedly attachable to the second bone anchor, the second connecting member portion including an outer cylindrical shape and an internal opening along an entire length thereof, the cord portion slidably positioned within and extending entirely through the internal opening, the second connecting member being in slidable relation with the cord portion before and after tensioning;
   c) an outer spacer being located between the first bone anchor and the second bone anchor and surrounding the cord portion and being in slidable relation therewith;
   d) a multi-part stiff end structure subassembly having a plurality of parts each engageable with and compressively securable to an outer end of the cord portion to hold the cord in tension, the multi-part stiff end structure subassembly comprising a non-threaded through-bore for slidably receiving the outer end of the cord portion therethrough; and
   e) an elastically compressible bumper having a through-bore, the cord portion extending through the bumper through-bore, the bumper located between the second bone anchor and the multi-part stiff end structure subassembly, and the bumper being in slidable engagement with the cord portion and cooperating to hold the cord portion in tension, and wherein the multi-part stiff end structure subassembly is compressively secured to the cord portion after tensioning.

35. The assembly of claim 34, wherein the second bone anchor is in slidable relation with the cord portion after being fixedly attached to the second connecting member.

36. The assembly of claim 34, wherein the second bone anchor is a polyaxial screw.

37. The assembly of claim 34, wherein the multi-part stiff end structure subassembly is at least partially releaseable to allow the cord portion to be further tensioned.

38. The assembly of claim 34, wherein the multi-part stiff end structure subassembly is securable to the outer end of the cord portion after the cord portion has been tensioned with a tool along the outer end thereof.

39. The assembly of claim 34, further comprising:
   a first and second bone anchor receiver coupled to the first connecting member and the second connecting member, respectfully.

40. A medical implant assembly comprising first and second bone anchors cooperating with a longitudinal connecting member, wherein the longitudinal connecting member comprises:
   a) a first substantially solid connecting member having a portion for attachment to the first bone anchor, the first solid connecting member including a first end thereof connected to a portion of a cord to be tensioned along the longitudinal connecting member;

b) a second connecting member having a portion for attachment to the second bone anchor, the second connecting member including an internal opening along an entire length thereof, the cord positioned within and extending entirely through the internal opening;

c) an outer spacer being located between the first bone anchor and the second bone anchor and surrounding the cord and being in slidable relation therewith;

d) a multi-part subassembly compressively securable to another portion of the cord opposite the portion connected to the first end to hold the cord in tension, the multi-part subassembly comprising a non-threaded through-bore for receiving the cord other portion therethrough; and e) an elastically compressed bumper having a through-bore, the cord portion extending through the bumper through-bore, the bumper located between the second bone anchor and the multi-part subassembly, and the bumper being in slidable engagement with the cord and cooperating to hold the cord in tension, and wherein the multi-part subassembly is secured to the cord portion after tensioning.

41. The assembly of claim 40, wherein at least one of the first bone anchor or the second bone anchor is a polyaxial screw.

42. The assembly of claim 40, wherein the multi-part subassembly is at least partially releaseable with respect to the cord so as to be able to re-tension the cord.

43. The assembly of claim 40, wherein the multi-part subassembly is securable to the cord portion after the longitudinal connecting member is attached to the first and second bone anchors and the cord is tensioned.

44. The assembly of claim 40, further comprising:
a first bone anchor receiver coupled to the first connecting member, wherein the entire cord is positioned entirely outside of the first bone anchor receiver.

45. A medical implant assembly comprising a plurality of bone anchors connected to a spine of a patient, the plurality of bone anchors cooperating with a longitudinal connecting member, wherein the longitudinal connecting member comprises:

a) a substantially solid first connecting member having a portion for attachment to a first bone anchor of the plurality of bone anchors, the first connecting member including a first end thereof connected to a tensionable cord elongated by tensioning to a length;

b) a second connecting member including an internal opening along an entire length thereof and having a portion for attachment to a second bone anchor of the plurality of bone anchors, the second connecting member being in slidable relation with the cord before and after tensioning, the cord positioned within and extending entirely through the internal opening;

c) an outer spacer being located between the first and second bone anchors and surrounding the cord and being in slidable relation therewith;

d) a multi-part stiff ring subassembly compressively securable to the cord to hold the cord in tension, the multi-part stiff ring subassembly comprising a non-threaded closed through-bore for directly engaging and slidably receiving the cord therethrough; and e) an elastically compressed bumper having a through-bore, the cord extending through the bumper through-bore, the bumper located between the second bone anchor and the multi-part stiff ring subassembly, and the bumper being at least initially in slidable engagement with the cord, the bumper being in compressive engagement with the multi-part stiff ring subassembly.

46. The assembly of claim 45, wherein the multi-part stiff ring subassembly is releaseable to allow the cord to be further tensioned.

47. The assembly of claim 45, further comprising:
a first bone anchor receiver coupled to the substantially solid first connecting member, the cord positioned entirely outside of the first bone anchor receiver.

48. A medical implant assembly comprising a bone anchor and a pivotal bone screw, the bone anchor and pivotal bone screw cooperating with a longitudinal connecting member, wherein the longitudinal connecting member comprises:

a) a substantially solid first connecting member having a portion for attachment to the bone anchor, the first connecting member including a first end thereof connected to a tensionable cord;

b) a second connecting member having a portion for attachment to the pivotal bone screw, the second connecting member including an internal opening along an entire length thereof, the cord positioned within and extending entirely through the internal opening;

c) an outer spacer located between the bone anchor and the pivotal bone screw and surrounding the cord and being in slidable relation therewith;

d) a multi-part stiff end structure having a plurality of parts securable to the cord to hold the cord in tension, such that the plurality of parts no longer have a slidable relationship with respect to the cord, wherein the multi-part stiff end structure has a part with a cylindrically shaped through-bore with the cord extending therethrough and engaged therewith, the multi-part stiff end structure having a non-rotating relationship relative to the cord and with respect to securing the multi-part stiff end structure to the cord so as to hold the cord in tension by compressing the cord against the through-bore; and e) an elastically compressible bumper having a through-bore, the cord extending through the bumper through-bore, the bumper located between the pivotal bone screw and the multi-part stiff end structure, the bumper initially being in slidable engagement with the cord, the bumper being positioned substantially outside of the second connecting member, and wherein the multi-part stiff end structure is secured to the cord after tensioning.

49. A medical implant assembly comprising first and second bone anchors, the first and second bone anchors cooperating with a longitudinal connecting member, wherein the longitudinal connecting member comprises:

a) a first connecting member portion attachable to the first bone anchor, the first connecting member portion having an internal opening along an entire length thereof, the connecting member portion at least partially positionable within and fixedly securable to the first bone anchor;

b) a tensionable cord positioned within and extending entirely through the internal opening and tensioned to a stable length, the first connecting member portion being in slidable relation with respect to the cord before and after cord tensioning; and c) a multi-part stiff end structure fixedly securable to the cord, wherein the multi-part stiff end structure has a smooth through-bore with the cord extending therethrough, the multi-part stiff end structure having a part with a non-rotating relationship relative to the cord and with respect to securing the multi-part stiff end structure to the cord so as to hold the cord in tension by compression of the cord against the through-bore after the cord is tensioned.

50. A medical implant assembly comprising first and second bone anchors cooperating with a longitudinal connecting member, wherein the longitudinal connecting member comprises:
    a) a first connecting member having a portion for attachment to the first bone anchor, the first connecting member including a first end thereof connected to a first end portion of a cord tensioned to a length;
    b) a second connecting member having a portion for attachment to the second bone anchor, the second connecting member including an internal opening along an entire length thereof, the cord slidably positioned within and extending entirely through the internal opening, the second connecting member being in slidable relation with the cord before and after tensioning;
    c) an outer spacer being located between the first bone anchor and the second bone anchor and surrounding the cord and being in slidable relation therewith;
    d) a multi-part stiff end structure subassembly securable to a second end portion of the cord after tensioning, wherein the multi-part stiff end structure subassembly includes a through-bore comprising a circumferentially extending inner surface with the second end portion of the cord extending therethrough, the multi-part stiff end structure subassembly being slidable along the cord while being tensioned with a non-rotating advancement on the cord toward the second connecting member prior to securing the multi-part stiff end structure subassembly to the cord so as to hold the second end portion of the cord in tension after tensioning; and
    e) an elastically compressible bumper having a through-bore, the cord portion extending through the bumper through-bore, the bumper located between the second bone anchor and the multi-part stiff end structure subassembly, and the bumper being in slidable engagement with the cord and cooperating to hold the cord in tension, and wherein the cord is tensioned prior to the longitudinal connecting member being attached to the first and second bone anchors.

51. A medical implant assembly comprising first and second bone anchors cooperating with a longitudinal connecting member, wherein the longitudinal connecting member comprises:
    a) a substantially solid first connecting member having a portion for attachment to the first bone anchor, the first connecting member including a first end thereof connected to a cord portion to be tensioned within the assembly;
    b) a second connecting member having a portion for attachment to the second bone anchor, the second connecting member including an internal opening along an entire length thereof, the cord portion positioned within and extending entirely through the internal opening;
    c) an outer spacer being located between the first bone anchor and the second bone anchor and surrounding the cord portion and being in slidable relation therewith;
    d) a multi-part subassembly securable to the cord portion after tensioning, wherein the multi-part subassembly has a non-threaded through-bore with the cord portion extending therethrough, the multi-part subassembly through-bore being slidable along the cord portion when tensioned and prior to being secured to the cord portion so as to hold the cord portion in tension by compression of the cord portion against the through-bore; and
    e) an elastically compressed bumper having a through-bore, the cord portion extending through the bumper through-bore, the bumper located between the second bone anchor and the multi-part subassembly, and the bumper being in slidable engagement with the cord portion and cooperating to provide tension in the cord after the multi-part subassembly is secured thereto.

52. A medical implant assembly comprising at least a pair of bone anchors connected to a spine of a patient, the of bone anchors cooperating with a longitudinal connecting member, wherein the longitudinal connecting member comprises:
    a) a substantially solid first connecting member having a portion for attachment to a first bone anchor of the pair of bone anchors, the first connecting member including a first end thereof connected to a tensionable cord elongated by tensioning to a length with a tool;
    b) a second connecting member including an internal opening along an entire length thereof and having a portion for attachment to a second bone anchor of the pair of bone anchors, after tensioning of the cord, the second connecting member being in slidable relation with the cord, the cord positioned within and extending entirely through the internal opening;
    c) an outer spacer being located between the pair of bone anchors and surrounding the cord and being in slidable relation therewith;
    d) a multi-part stiff ring subassembly securable to the cord after tensioning, wherein the multi-part stiff ring subassembly has a non-threaded through-bore with the cord slidably extending therethrough prior to securement, the multi-part stiff ring subassembly having a non-rotating relationship relative to the cord and with respect to securing the multi-part stiff ring subassembly to the cord, the multi-part stiff ring subassembly configured to compress the cord against the through-bore so as to hold the cord in tension; and
    e) an elastically compressed bumper having a through-bore, the cord extending through the bumper through-bore, the bumper located between the second connecting member and the multi-part stiff ring subassembly, and the bumper being at least initially in slidable engagement with the cord, the bumper being in compressive engagement with the multi-part stiff ring subassembly and the second connecting member after the cord is tensioned.

* * * * *

UNITED STATES PATENT AND TRADEMARK OFFICE
CERTIFICATE OF CORRECTION

PATENT NO.       : 10,258,382 B2
APPLICATION NO.  : 12/148465
DATED            : April 16, 2019
INVENTOR(S)      : Roger P. Jackson Page 1 of 1

It is certified that error appears in the above-identified patent and that said Letters Patent is hereby corrected as shown below:

In the Claims

- In Claim 22, Column 21, Line 34, delete the second occurrence of "the" following 'as'.

- In Claim 40, Column 23, Line 20, delete "portion".

- In Claim 50, Column 25, Line 41, delete "portion".

- In Claim 51, Column 26, Line 20, insert --portion-- following 'cord'.

- In Claim 52, Column 26, Line 23, insert --pair-- following 'the'.

Signed and Sealed this
Fifteenth Day of June, 2021

Drew Hirshfeld
*Performing the Functions and Duties of the*
*Under Secretary of Commerce for Intellectual Property and*
*Director of the United States Patent and Trademark Office*